(12) United States Patent
Forsell

(10) Patent No.: US 11,278,404 B2
(45) Date of Patent: *Mar. 22, 2022

(54) ARTIFICIAL VALVE

(71) Applicant: Peter Forsell, Bouveret (CH)

(72) Inventor: Peter Forsell, Bouveret (CH)

(*) Notice: Subject to any disclaimer, the term of this patent is extended or adjusted under 35 U.S.C. 154(b) by 0 days.

This patent is subject to a terminal disclaimer.

(21) Appl. No.: 16/290,982

(22) Filed: Mar. 4, 2019

(65) Prior Publication Data

US 2020/0188103 A1 Jun. 18, 2020

Related U.S. Application Data

(63) Continuation of application No. 13/123,151, filed as application No. PCT/SE2009/051148 on Oct. 12, 2009, now Pat. No. 10,219,898.

(60) Provisional application No. 61/213,157, filed on May 12, 2009.

(30) Foreign Application Priority Data

Oct. 10, 2008 (SE) ..................... 0802157-8

(51) Int. Cl.
A61F 2/24 (2006.01)

(52) U.S. Cl.
CPC ...... *A61F 2/2421* (2013.01); *A61F 2210/009* (2013.01); *A61F 2250/0001* (2013.01)

(58) Field of Classification Search
CPC .................................................. A61F 2/2421
See application file for complete search history.

(56) References Cited

U.S. PATENT DOCUMENTS

| 5,135,538 | A | 8/1992 | Pawlak | |
| 2003/0225311 | A1* | 12/2003 | Sayet | A61F 2/0036 600/29 |
| 2005/0148925 | A1 | 7/2005 | Rottenberg | |

* cited by examiner

Primary Examiner — Leslie Lopez

(57) ABSTRACT

An artificial valve for implantation in a mammal body, in or adjacent to a mammal blood vessel, the artificial valve comprising a casing and a closing mechanism, with at least part of said closing mechanism being a first moving part adapted to make movements relative to said casing. The movements are movements to assume a fully open and a fully closed position for opening and closing, respectively, the blood flow through said blood vessel, as well as at least one position in between said fully open and fully closed positions. The first moving part is adapted to receive energy for at least one of its movements at least in part from an energy device which is also comprised in the artificial valve and arranged to be placed external to said blood vessel.

14 Claims, 32 Drawing Sheets

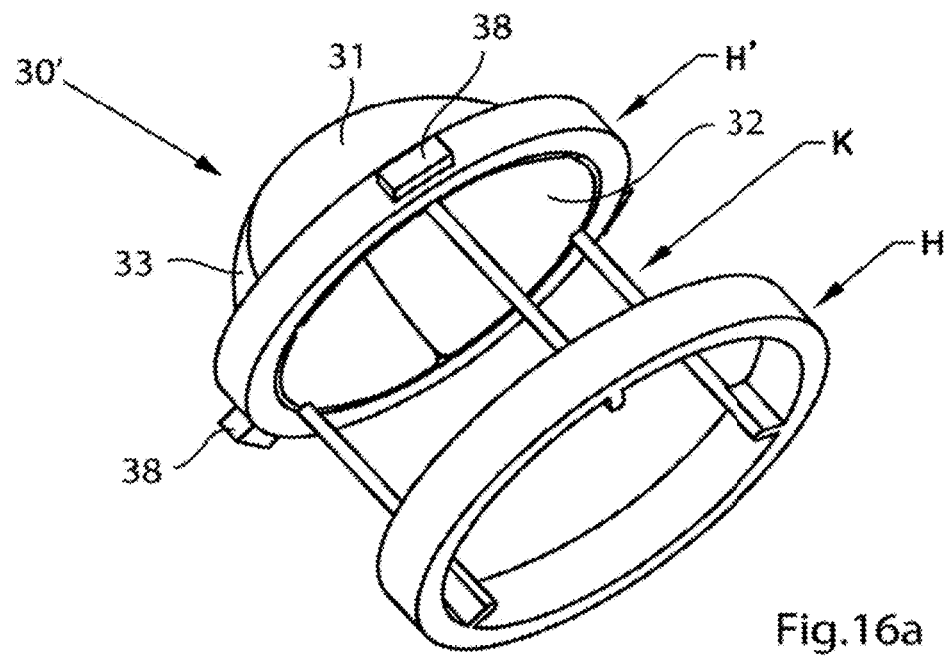
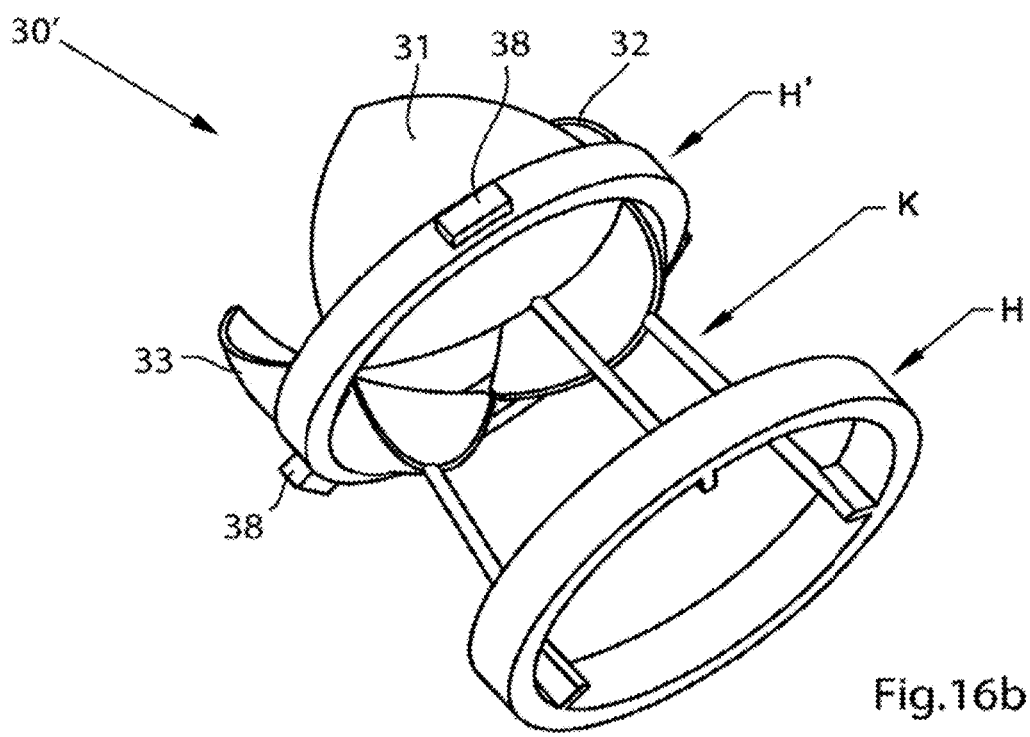

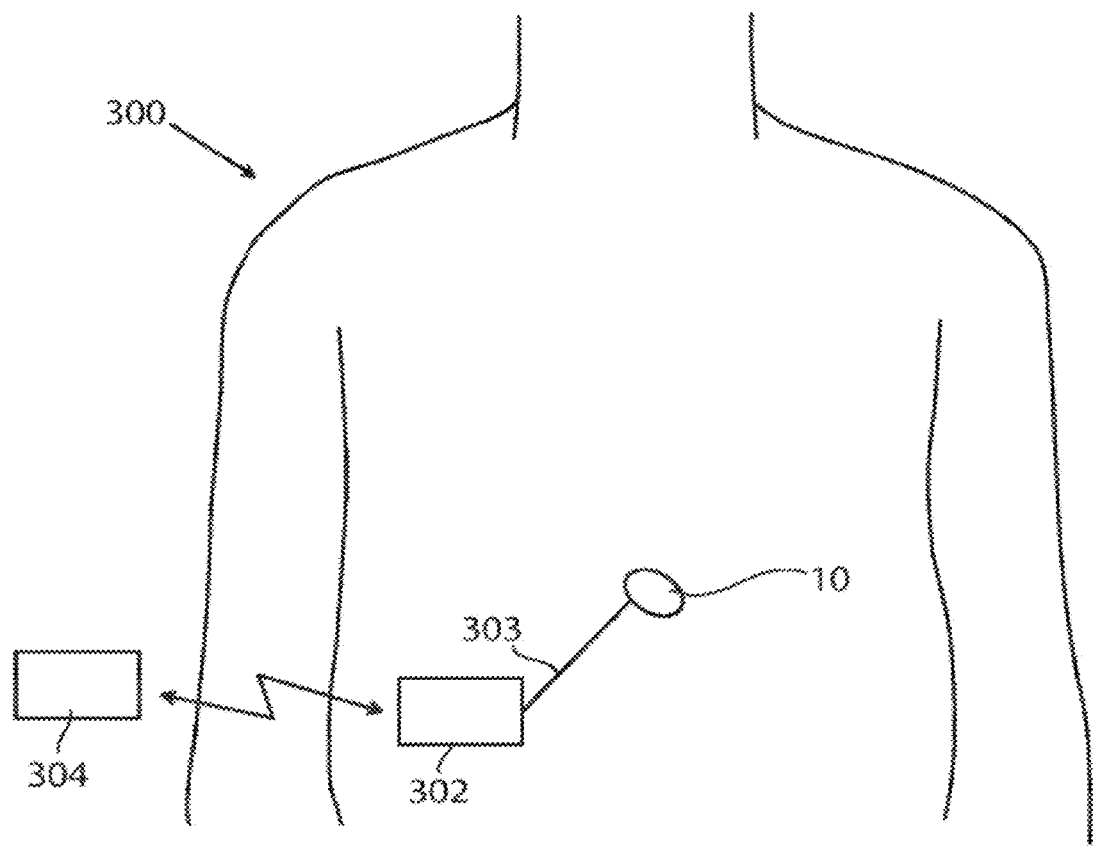

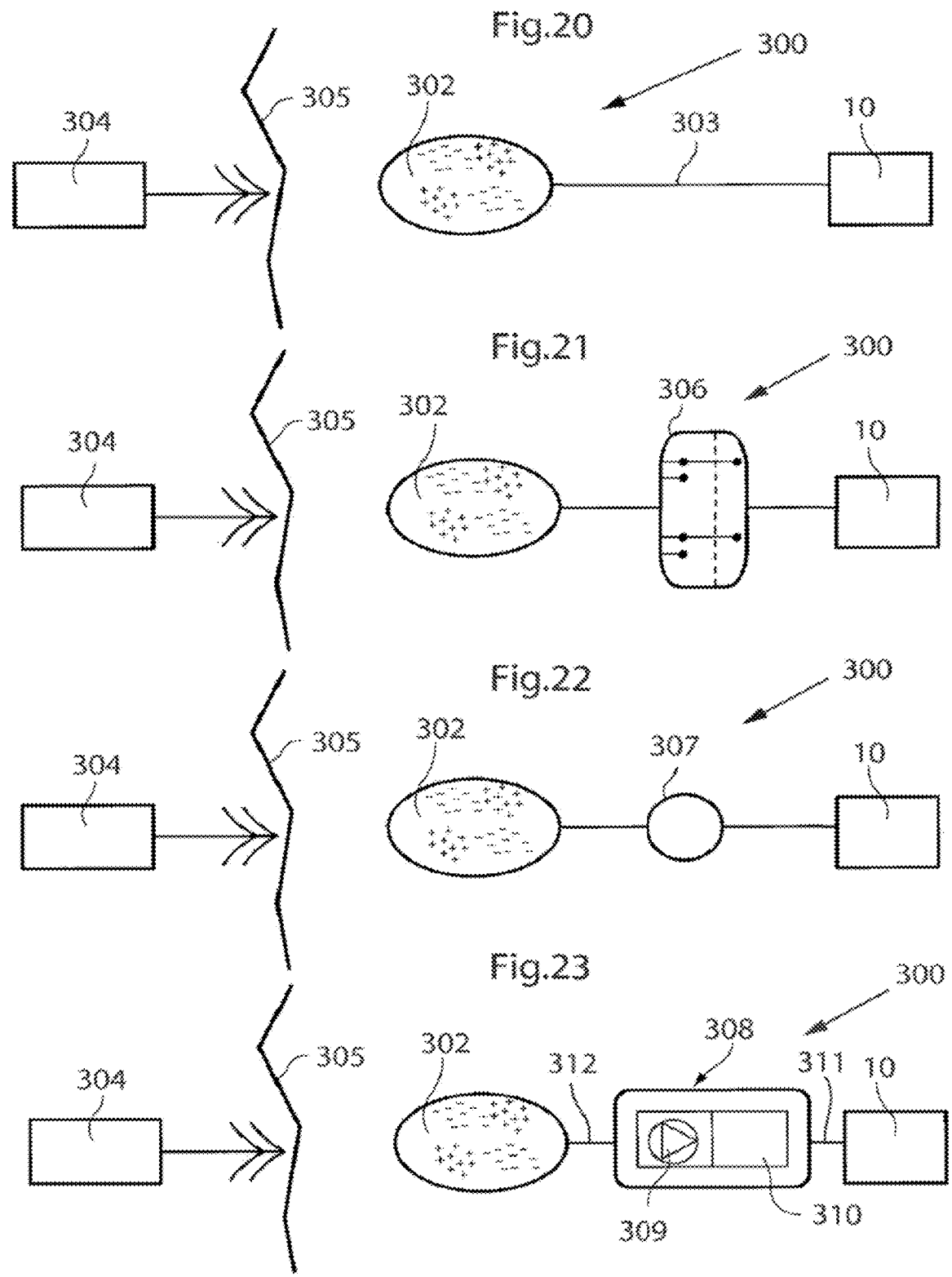

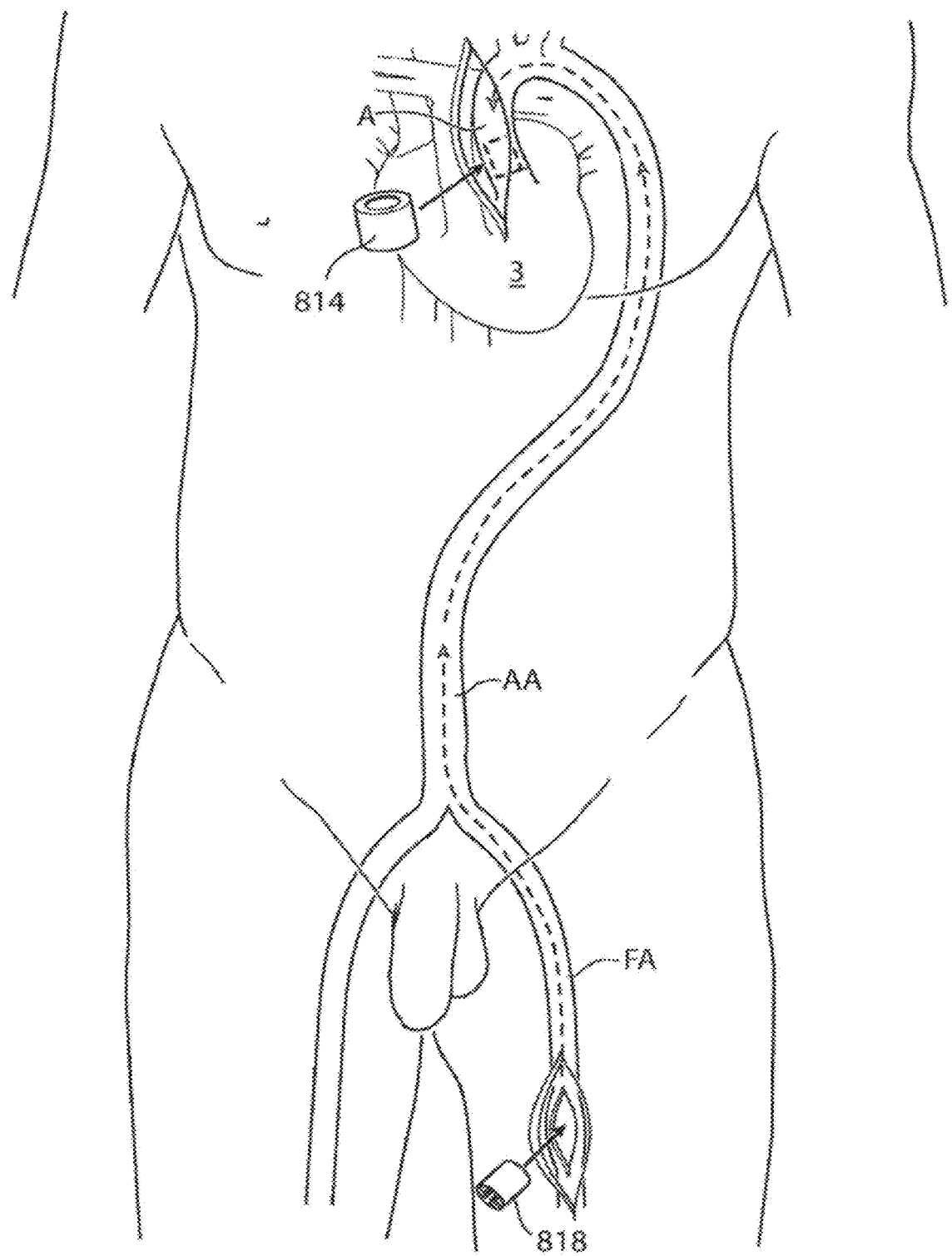

ARTIFICIAL VALVE

TECHNICAL FIELD

The present invention discloses an artificial valve for implantation in a mammal body, in or adjacent to a mammal blood vessel. The valve of the invention comprises a casing and a closing mechanism, and at least part of the closing mechanism is a moving part adapted to make movements relative to the casing.

BACKGROUND

Artificial valves for implantation into mammal blood vessels are used in order to replace existing valves in the circulatory system of a mammal. When implanted in the circulatory system of a mammal, such valves are used to regulate the flow of blood in the mammal by means of closing or opening the blood flow in the vessel, which is accomplished by letting one or more moving parts in the valve assume a closed position or to move to assume an open position.

SUMMARY

It is an object of the present invention to provide an artificial valve for implantation into a mammal blood vessel which overcomes drawbacks of known such artificial valves.

This object of the present invention is achieved by means of an artificial valve for implantation in a mammal body, in or adjacent to a mammal blood vessel. The artificial valve of the invention comprises a casing and a closing mechanism, and at least part of the closing mechanism is a first moving part which is adapted to make movements relative to the casing. The movements are movements to assume an open and a closed position for opening and closing, respectively, the blood flow through said blood vessel, as well as to positions in between said open and closed positions. The first moving part is adapted to receive energy for at least one of its movements at least in part from an energy device which is also comprised in the artificial valve and arranged to be placed external to said blood vessel.

In one embodiment of the valve of the invention, the closing mechanism is arranged to cause the first moving part to move between two desired positions by means of giving the moving part kinetic energy in a plurality of steps in its movement between said two desired positions.

In one embodiment of the valve of the invention, the closing mechanism comprises one or more magnets adapted to receive energy from the energy device as a first pulse, said one or more magnets further being adapted to receive one or more additional pulses with a time delay in relation to said first pulse to cause said kinetic movement of said first valve member.

In one embodiment of the valve of the invention, the closing mechanism comprises at least two magnets, said closing mechanism being adapted to receive said additional pulses to affect a different magnet or a different group of magnets than said first pulse.

In one embodiment of the valve of the invention, the closing mechanism comprises a coil which is adapted to be energized so as to cause said movement of the closing mechanism.

In one embodiment of the valve of the invention, the closing mechanism comprises a coil which is adapted to be energized stepwise with two or more energy pulses so as to cause said movement of the closing mechanism.

In one embodiment of the valve of the invention, the closing mechanism comprises a plurality of coils which are adapted to be energized stepwise so as to cause said movement of the closing mechanism.

In one embodiment of the valve of the invention, at least either the magnets or the coils are arranged at intervals in the casing along an intended path of movement of the moving part.

In one embodiment of the valve of the invention, the first moving part is adapted to move to assume an open or a closed position as well as positions in between said open and closed positions. Suitably, in this embodiment, the valve also comprises first and second hinges arranged in the casing, about which hinges the first moving part is arranged to be able to move to assume an open or a closed position as well as positions in between said open and closed positions.

In one embodiment, the closing mechanism of the valve also comprises a second moving part, and the first and second moving parts are adapted to move to assume a closed and an open position as well as to positions in between said open and closed positions, in order to close or limit the blood flow through the blood vessel. Suitably, in this embodiment, the first and second moving parts are movably hinged about respective first and second hinges in the casing, and can move about these hinges to assume an open or a closed position as well as positions in between said open and closed positions.

In one embodiment, the closing mechanism of the valve also comprises a second and a third moving part, and the first, second and third moving parts are adapted to move to assume a closed and an open position as well as positions in between said open and closed positions in order to close or limit the blood flow through the blood vessel. Suitably, in this embodiment, the first, second and third moving parts are movably hinged about respective first and second hinges in the casing, and can move about these hinges in order to assume an open or a closed position as well as positions in between said open and closed positions.

In one embodiment, the closing mechanism of the valve comprises an additional three or more moving parts, and the moving parts of the valve are adapted to move to assume a closed and an open position as well as positions in between said open and closed positions in order to close or limit the blood flow through the blood vessel. Suitably, in this embodiment, each of the moving parts is movably hinged about respective first and second hinges in said casing, and can move about these hinges in order to assume an open or a closed position as well as positions in between said open and closed positions.

Suitably, in the embodiments with two or more moving parts, the moving parts come together to form a cupola in the closed position, and also suitably, the first and second hinges of at least one of said moving parts are positioned at or adjacent to a meeting point of the moving parts. In addition, in these embodiments, the first and second hinges of at least one of said moving parts are placed at substantially opposite distal ends of said moving part along the casing.

In another embodiment, the closing mechanism of the valve of the invention comprises an elongated essentially flat plate which is adapted to, when the valve is arranged in or adjacent to an opening in said blood vessel, move into this opening in a direction which is essentially perpendicular to the blood vessel in order to limit or close the blood flow through said vessel.

In one embodiment with the plate, an outer wall of the casing is suitably concavely curved in order to essentially coincide with the outer shape of a blood vessel, and the curved outer wall also comprises an opening for the plate, through which opening the plate can move in its movements. The tolerance between the dimensions of the opening and the plate are then such that the movements of the plate are enabled, but also such that leakage of blood between the plate and the opening is essentially eliminated.

In the "plate embodiment", the casing also suitably comprises at least a first curved protruding part in order to surround at least part of the circumference of a blood vessel, in order to enable attachment of the valve to the blood vessel.

In another embodiment, the casing comprises at least a first and a second curved protruding part for surrounding at least part of the circumference of a blood vessel, in order to enable attachment of the valve to the blood vessel.

The valve of the "plate embodiment" can also, in one embodiment, comprise a detachable part for attachment to the casing or to one or more protruding parts of the casing, so that the valve will completely surround a blood vessel by means of at least one protruding part and said detachable part and/or by means of an outer wall of the valve.

In the plate embodiments, the valve of the invention can also comprise a biasing mechanism, for biasing the plate to an open position.

The valve of the invention also suitably comprises a receiving device for receiving a closing signal, and for supplying this closing signal to the closing mechanism, which in turn is adapted to close upon reception of said signal.

The closing signal may be received by the receiving device from a source external to the valve, or it may be received from a sensor which is comprised in the valve. In both of these embodiments, the signal is supplied as the result of a parameter reaching a certain threshold value at which the valve should initiate its closing movement.

BRIEF DESCRIPTION OF THE DRAWINGS

The invention will be described in more detail in the following, with reference to the appended drawings, in which

FIGS. 16a-b show various versions of a powered movement.

FIG. 19 illustrates a system for treating a disease, wherein the system includes an apparatus of the invention implanted in a patient.

FIGS. 20-34 schematically show various embodiments of the system for wirelessly powering the apparatus shown in FIG. 19.

FIGS. 49-52 illustrate an operation method of the invention.

DETAILED DESCRIPTION

The invention will be described in the following with reference to a human blood vessel, and may also be described below as being placed in a human heart. It should however be pointed out that these are merely examples given in order to facilitate the reader's understanding of the invention; the artificial valve of the invention can be used at more or less any point in the circulatory system of any mammal.

In addition, the artificial valve of the invention can be used in order to replace a biological valve, as an alternative to which it can be used in order to supplement a biological valve, or to create a "valve function" in a position where the body is normally not equipped with a valve function.

As has been mentioned above, the present invention discloses an artificial valve for implantation in a mammal body, in or adjacent to a mammal blood vessel. The valve of the invention comprises a casing and a closing mechanism, and at least part of the closing mechanism is a moving part which is adapted to make movements relative to the casing. These movements enable the moving part of the closing mechanism to assume an open and a closed position for opening and closing, respectively, the blood flow through the blood vessel, as well as to positions in between said open and closed positions.

The closing mechanism of the valve is adapted to be powered in its movements to the closed position in part or entirely by means of a power mechanism external to said blood vessel.

Figure 1A:
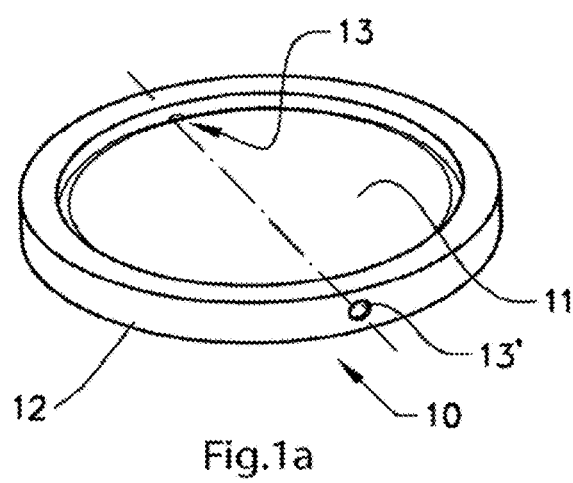
FIGS. 1a and 1b show side views of a first embodiment of the invention in an open and a closed position.

Before the powering of the closing mechanism is described in more detail, some embodiments of the closing mechanism as such will first be described. FIG. 1a shows a side view of a first embodiment 10 of an artificial valve of the invention. As seen in FIG. 1a, in this embodiment, the closing mechanism of the valve comprises a first moving part 11, suitably essentially shaped as a disc in order to enable the closing of a blood vessel. The valve 10 also comprises a casing 12 in which the moving part 11 is housed.

As is also shown in FIG. 1a, the casing 12 comprises a ring, which is shaped so that the disc 11 may rotate in the casing to assume open and closed positions, as well as positions in between said open and closed positions. In order to enable the rotation of the disc 11, the valve 10 also comprises first 13 and second 13' hinges arranged in the casing, about which hinges the disc can rotate. As will be realized, in the open position, shown in FIG. 1b, the disc 11 is essentially perpendicular to the casing 12, while it in the closed position is essentially aligned with an inner wall of the casing 12.

Figure 1B:
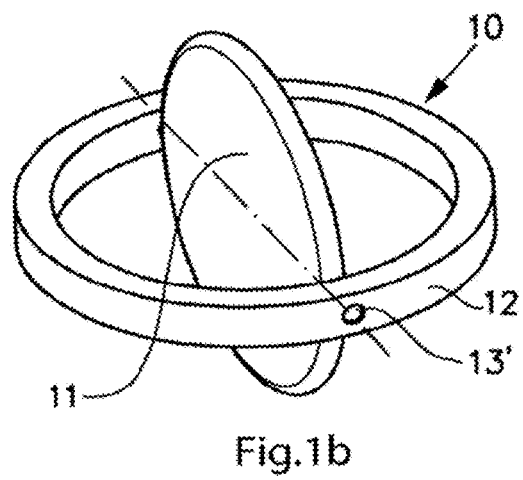

FIG. 1b shows a side view of the embodiment 10 in the open position.

Figure 2A:
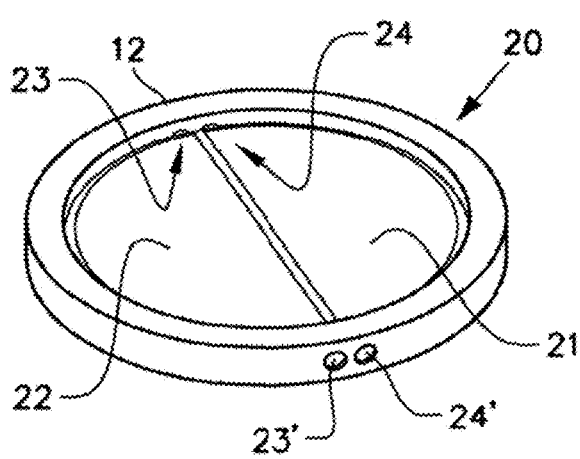
FIGS. 2a-2d show side views of a second and a third embodiment in open and a closed position.
Figure 2:
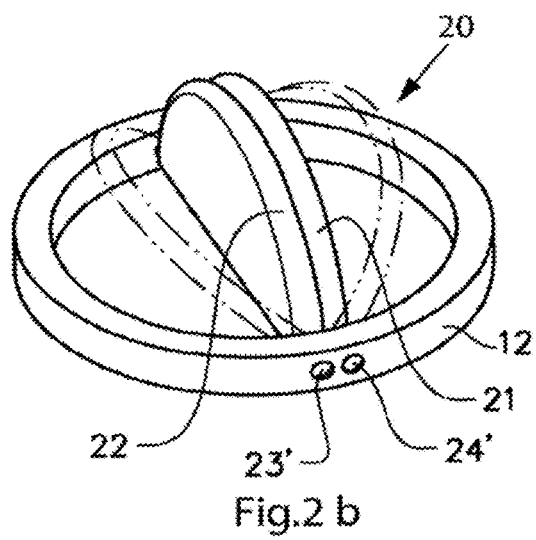

In a second embodiment 20, shown in a side view in FIG. 2a, the closing mechanism of the valve comprises a first 21 and a second 22 moving part, each of which moving part is movably hinged about respective first 23, 23' and second 24, 24', hinges in a ring-shaped casing 12.

The first 21 and second 22 parts can move about their respective hinges to assume a closed and an open position, as well as positions in between said open and closed positions in order to close or limit the blood flow through said blood vessel.

Figure 2C:
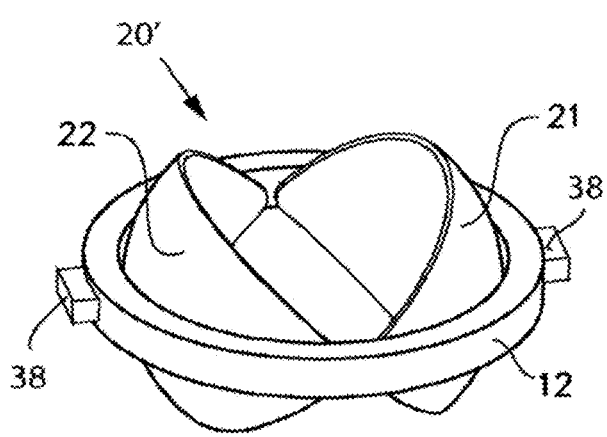
Figure 2D:
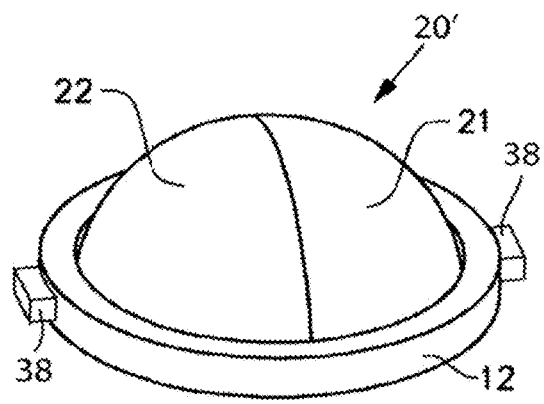

FIG. 2b shows the valve 20 in a side view. As can be seen here, the two parts 21 and 22 are essentially flat halves of a flat disc, while FIGS. 2c and 2d show an embodiment 20' in which the two moving parts 21, 22, come together to form a cupola in the closed position of the valve 20. FIGS. 2c and 2d also show parts 38 of a closing mechanism which will be described in more detail later in this text.

Figure 3A:
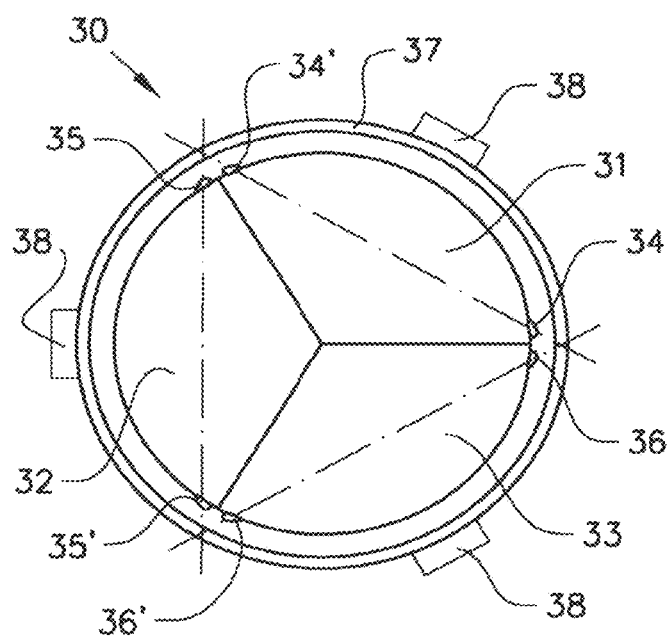
FIGS. 3a-3e show views of a fourth embodiment in various positions.

In a further embodiment 30 of the inventive valve, which is shown in a plan view in FIG. 3a, the closing mechanism of the valve comprises first 31, second 32 and third 33 moving parts, each of which is movably hinged about respective first 34, 35, 36 and second 34', 35', 36', hinges in a ring-shaped casing 37.

In this embodiment, the first 31, second 32 and third 33 moving parts can move about their respective hinges to assume a closed and an open position as well as positions in between said open and closed positions in order to close or limit the blood flow through said blood vessel, The words "open" and "closed" positions for the embodiments 20 and 30 of the valve should here be taken to mean that each moving part can assume a closed and an open position, but that each part needs to be in its closed position in order for the blood flow through a blood vessel to be closed, and that a maximally open valve is achieved when each moving part is in its open position.

Figure 3B:
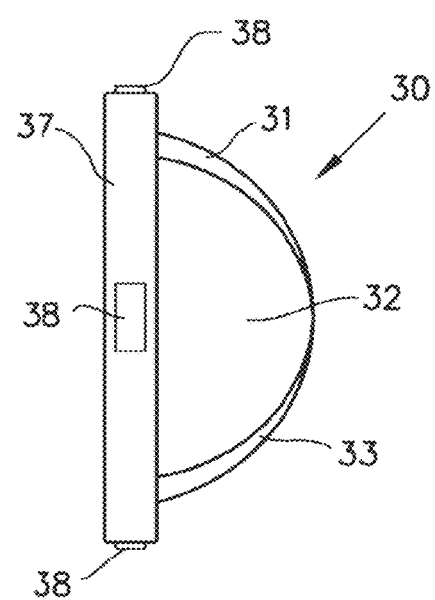
Figure 3C:
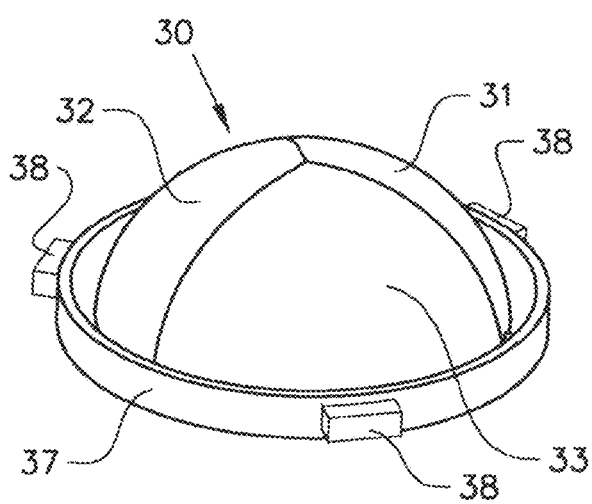

As shown in side views in FIGS. 3b and 3c, in similarity to the embodiment 20 shown in FIGS. 2c and 2d, in the "three part embodiment" 30, the moving parts suitably come together to form a cupola in the closed position.

Figure 3D:
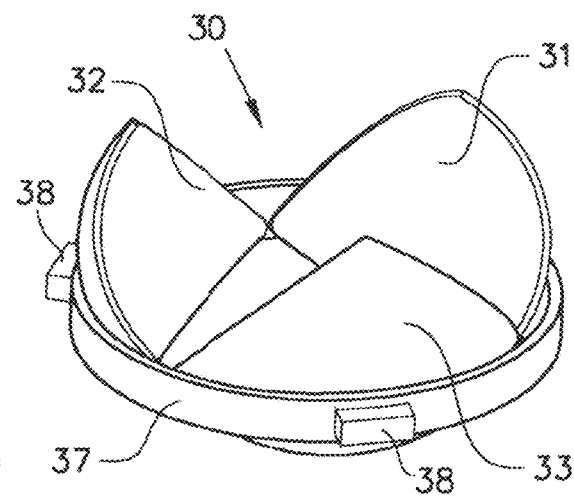
Figure 3E:

FIG. 3d shows the embodiment 30 in the open position, and FIG. 3e shows one of the cupola parts 31 with its hinges 34, 34'.

As shown in the views of FIGS. 2a and 3a, in the embodiments 20 and 30, the first and second hinges of at least one of the moving parts of the valve of those embodiments are positioned at or adjacent to a meeting point of the moving parts.

Also suitably, which can also be seen in the views of FIGS. 2a and 3a, the first and second hinges of at least one of the moving parts of the valve of those embodiments are placed at substantially opposite distal ends of the moving part along the casing.

This positioning of the hinges allows for a smoother and easier movement of the moving parts of the valve, as opposed to the hinges of traditional valves, which are usually placed at a centre position of the moving part.

As has emerged from the description above, the valve of the invention features "powered closing", i.e. powered movement of the closing parts, but as an alternative, the closing mechanism of the valve in the embodiments 20 and 30 is also adapted to be at least partly closed by the flow of blood, so that the flow of blood will bring the closing mechanism with it in a closing movement. In other words, the flow of blood in the "back direction" can in such embodiments assist the powered mechanism of the valve in closing the valve. This can also be seen as letting the closing mechanism be adapted to be at least partly closed by blood pressure of a certain level.

Figure 4A:
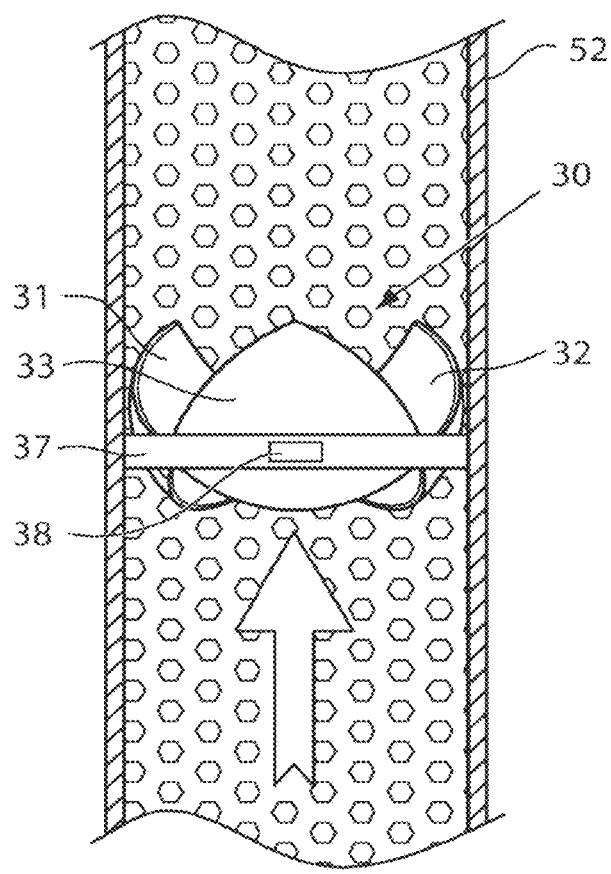
FIGS. 4a and 4b show a valve of the invention implanted in a blood vessel.
Figure 4B:
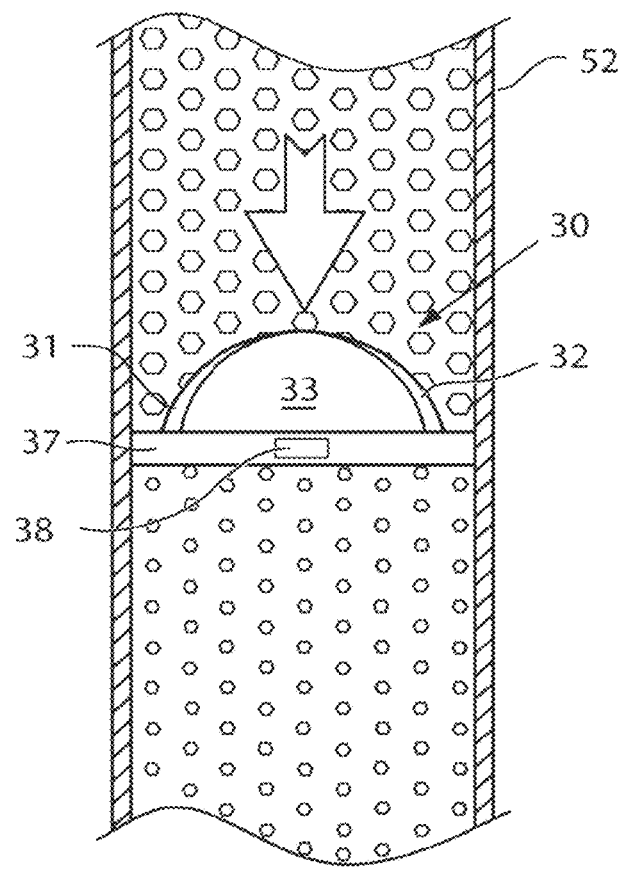

FIGS. 4a and 4b show the valve 30 in a blood vessel 52, in the open (FIG. 4a) and closed (FIG. 4b) positions. It can be gleaned from these drawings (as also indicated by means of an arrow in the blood vessel 52) that in some embodiments, the flow of blood will be used to assist in the closing movement of the moving parts, as well as possibly (FIG. 4a) also in the opening movement of the moving parts.

Some different way of how the closing mechanism of the embodiments can be powered in its movements will now be described, before a different version of the valve of the invention is described.

Figure 18:
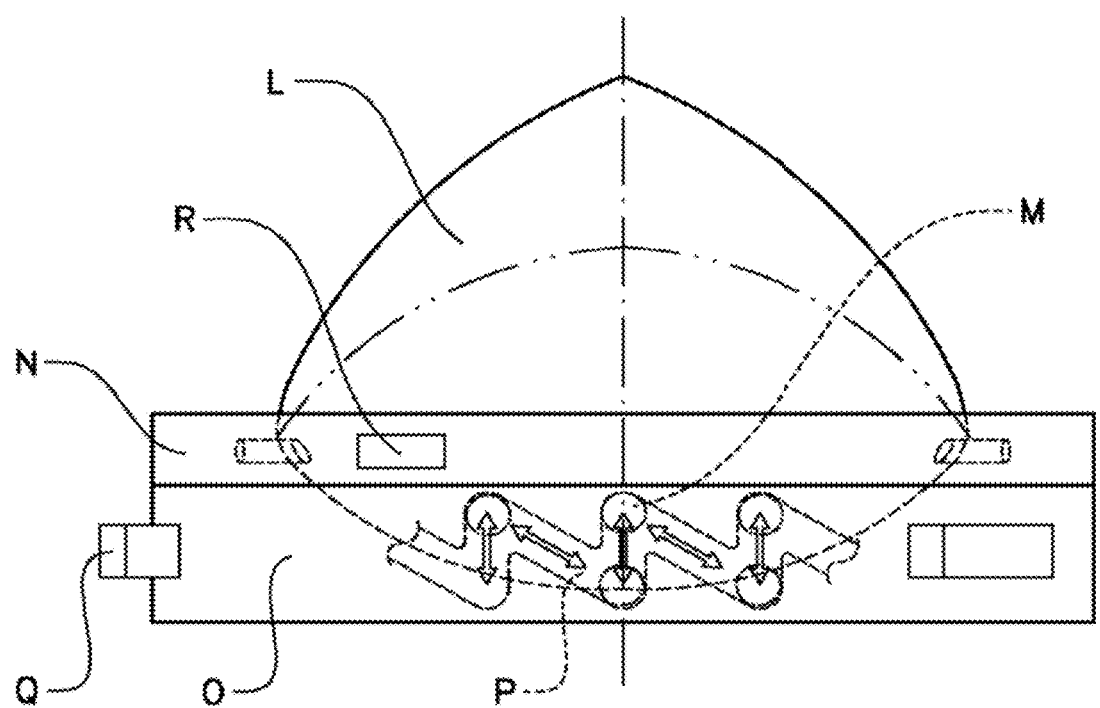
FIG. 18 shows a version of a powered movement.

The powering of the movements of the closing mechanism is shown in FIGS. 16-18 below, and is based on the casing having a first H and second H' casing part, with the first part being displaceable in relation to the second part in order to cause the opening and/or closing movement. Suitably, the first H and second H' casing parts each comprise a ring, with the two rings being concentric to each other, and with one of the first or second rings being adapted to move in relation to the other part in order to cause the closing and/or opening movement.

As can be seen in FIGS. 16a and 16b, the two parts H' and H of the casing each constitute rings and can be made to move away from each other or towards each other, i.e. essentially in the direction of the "axis" of a blood vessel. Suitably, only one of the casing parts should be made to move.

In the embodiment of FIGS. 16a and 16b, the ring H, which is the most distant from the moving parts of the cupola, has one end of each of three mechanical elements K, for example three pins, attached to it, with the other ends of the pins being attached to one each of the moving parts of the cupola.

As the distance between the two parts of the casing, H and H', is made to increase or decrease, by means of, for example, magnets and coils, the pins will cause the cupola parts to move about their hinges and open, FIG. 16b, or close, FIG. 16a.

FIGS. 17a-17d show another embodiment in which the casing parts are also concentric rings H', H. However, in this embodiment, the opening and/or closing movement of the cupola parts is obtained by letting the rings rotate in relation to each other, suitably with only one of the rings rotating.

As can be seen in FIGS. 17a-17d, the ring H which can be made to rotate, for example by means of interaction between springs on one ring and coils on the other, comprises three pins, J, which can move in corresponding openings I of the other ring H'.

As can also be seen in FIGS. 17a-17d, the cupola parts comprise a groove N (not a through-going groove though) in which the pin J can run. The groove N is slanted in the cupola part, so that rotation of the ring H with the pins J will cause the cupola parts to open or close, depending on the direction of rotation of the ring H.

FIG. 18 shows another embodiment of how the cupola parts may be made to open and/or close actively as well as passively; in this embodiment as well, the casing comprises an upper N and a lower O ring shaped part, which are essentially concentric.

One of the ring shaped parts, O, comprises a groove P, which consists of vertical and slanted parts, in an alternating fashion. A pin M from each cupola part runs in this groove P. If the blood pressure increases, the cupola part will open, since the pin will move in a vertical (i.e. essentially parallel with the extension of a blood vessel) part of the groove, and can also be closed when the blood begins to flow in the reverse direction, i.e. during the diastolic phase of the heart.

However, if the ring O with the groove P in it is made to rotate, the pin will be forced to move in or by a slanted part of the groove, which will also cause the cupola part to perform a closing or opening movement, depending on the direction of rotation of the ring. A mechanism for making the ring O rotate is indicated as Q in FIG. 18.

Figure 47:
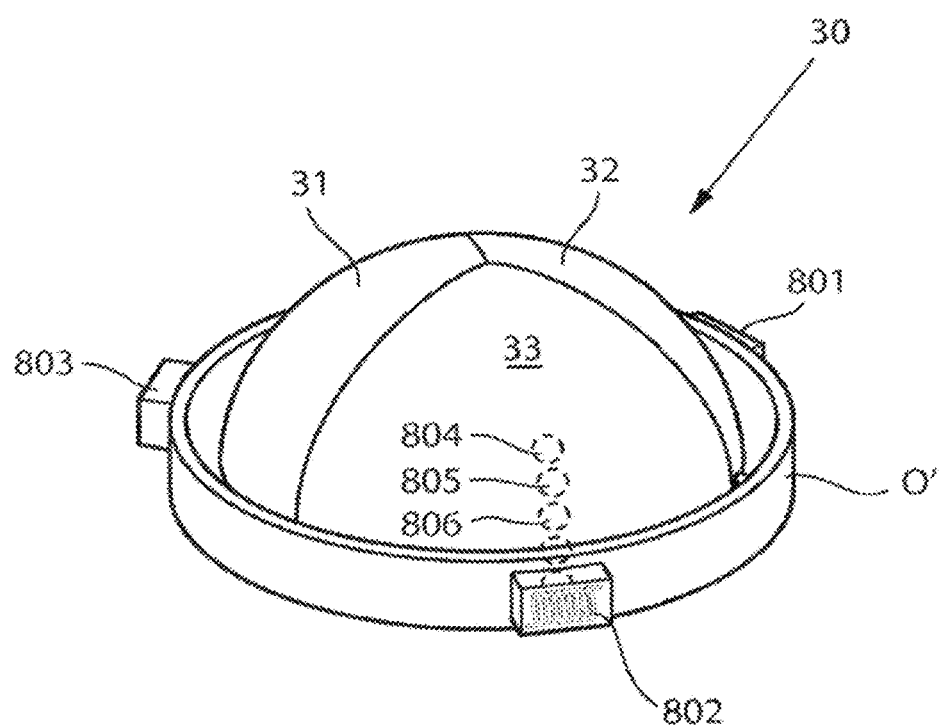
FIGS. 47 and 48a-b show an embodiment of the invention.

FIG. 47 shows a further embodiment for powering the "cupola embodiments": a cupola embodiment with three parts, 31, 32, and 33 is shown as an example of such an embodiment. On each cupola part, there is arranged a "ladder" of magnets 804-806 (shown only on cupola part 33), i.e. magnets arranged in line essentially in the direction of movement of the cupola part.

On a ring O' which is part of the casing of the valve 30, there is arranged a coil 801, 802, 803, which is positioned so that energizing (by means of AC current/voltage) the coil will affect one or more of the magnets on the corresponding cupola part, and will thus cause the cupola part to perform an opening or closing movement. Naturally, the coil can be energized to affect to the magnets step-wise, i.e. one at a time as cupola part moves past the coil.

An alternative embodiment of the invention, shown in FIGS. 5a-10d, comprises one or more of the following features, singly or in combination:

The first moving part of the closing mechanism is adapted to assume a position at least partly placed outside of the blood vessel when the valve is in a non-closed position in the mammal body.

The first moving part is adapted to, when the valve is arranged in or adjacent to an opening in said blood vessel 52, move in an opening in the blood vessel to limit or close the blood flow through said vessel, with at least a portion of said first moving part 51 assuming a position external to said blood vessel in a non-closed position.

The first moving part is arranged to move in said opening in a direction which is essentially perpendicular to the extension of the blood vessel.

The first moving part comprises an elongated essentially flat plate 51 which is adapted to, when the valve is arranged in or adjacent to an opening in said blood vessel 52, move in a direction essentially perpendicular to said blood vessel to limit or close the blood flow through said vessel, with at least a portion of said first moving part 51 assuming a position external to said blood vessel in a non-closed position.

The closing mechanism is housed in the casing 61, with the first moving part 51 being adapted to protrude from the housing 61 in its closing movements.

The valve 50 also comprises a biasing mechanism 82 for biasing the plate 51 to an open position.

The biasing mechanism comprises a spring mechanism 82.

The first moving part 51 is given a curved or semicircular shape at the end 53 of the part which will be the first to enter said opening in the blood vessel during a closing movement of the first moving part 51, whereby the first moving part is adapted to fit against a distal inner wall of the blood vessel in order to close or limit the passage of blood in said blood vessel.

An outer wall 62 of the casing 61 is concavely curved to essentially coincide with the outer shape of a blood vessel, said curved outer wall 62 also comprising an opening 63 for the first moving part 51, through which opening it can move in its movements, with the tolerance between the dimensions of the opening and the first moving part being such that the movements are enabled, but also such that leakage of blood between the first moving part and the opening is essentially eliminated.

The casing 61 also comprises at least a first curved protruding part 64, 65 for surrounding at least part of the circumference of a blood vessel 52, for attachment of the valve to said blood vessel.

The casing 61 also comprises at least first 64 and second 65 curved protruding parts for surrounding at least part of the circumference of a blood vessel, for attachment of the valve to said blood vessel.

The protruding part or parts, together with said concave outer wall, are adapted to be attached to the blood vessel by means of a vascular graft 82.

The valve 50 also comprises a detachable part 71 for attachment to one or more protruding part 64, 65 or to the casing 61, so that the valve may completely surround a blood vessel by means of at least one protruding part and said detachable part and/or by means of an outer wall of the valve.

The valve 50 also comprises a protruding guide 81 for guiding the movements of the plate 51 in the blood vessel, said guide 81 thus being intended for arrangement inside the blood vessel and being essentially shaped to coincide with the outer form of the plate 51, with a certain tolerance to enable the plate 51 to move in the guide.

Figure 5A:
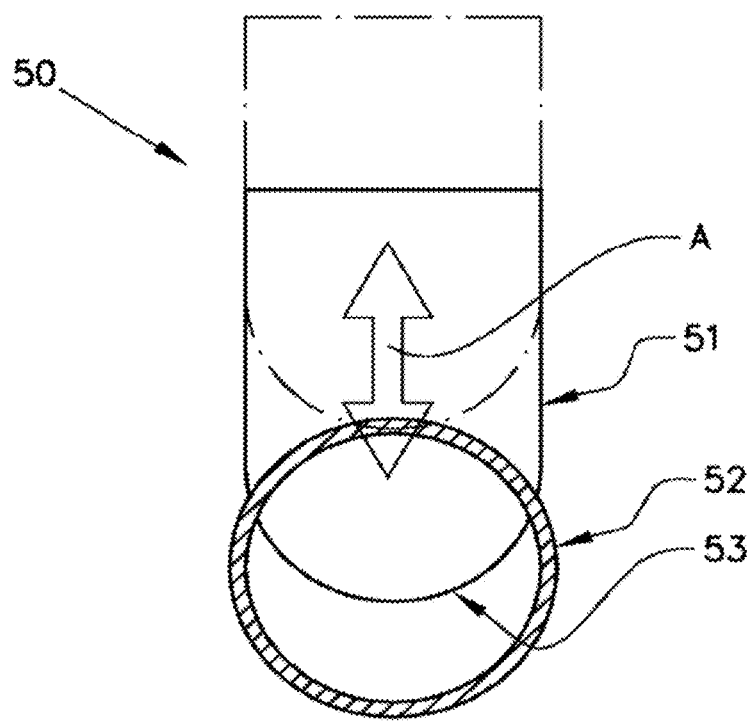
FIGS. 5a and 5b show a further embodiment of the invention together with a blood vessel.

This embodiment 50 is shown in one aspect in a plan view in FIG. 5a, together with a blood vessel 52; the closing mechanism of the valve comprises an elongated and essentially flat plate 51 which is adapted to, when the valve 50 is arranged in or adjacent to an opening in the blood vessel 52, move into this opening in a direction which is essentially perpendicular to the blood vessel in order to limit or close the blood flow through said vessel. The direction of movement of the plate 51 is indicated by means of an arrow "A" in FIG. 5a.

As can be seen in FIG. 5a, in one embodiment, the flat plate 51 is given a curved or semicircular shape at the end 53 of the plate 51 which will be the first to enter an opening in the blood vessel 52 during a closing movement, and by means of the curved shape of the end 53, the plate 51 is then adapted to fit against a distal inner wall of the blood vessel 52 in order to close or limit the passage of blood in said blood vessel.

Figure 5B:
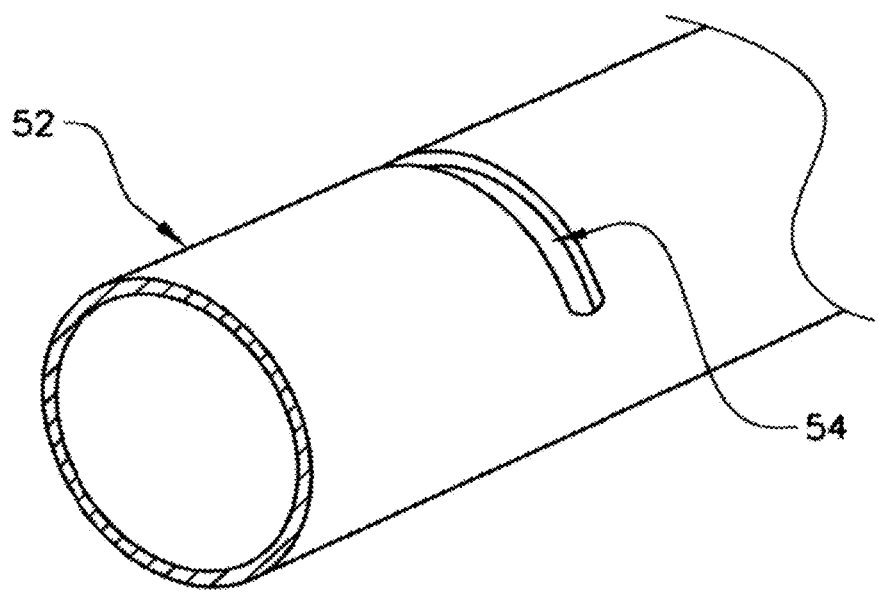

The blood vessel 52 is shown in a perspective view in FIG. 5b, together with an opening 54 which is made in the blood vessel in order to admit the plate 51.

Figure 6:
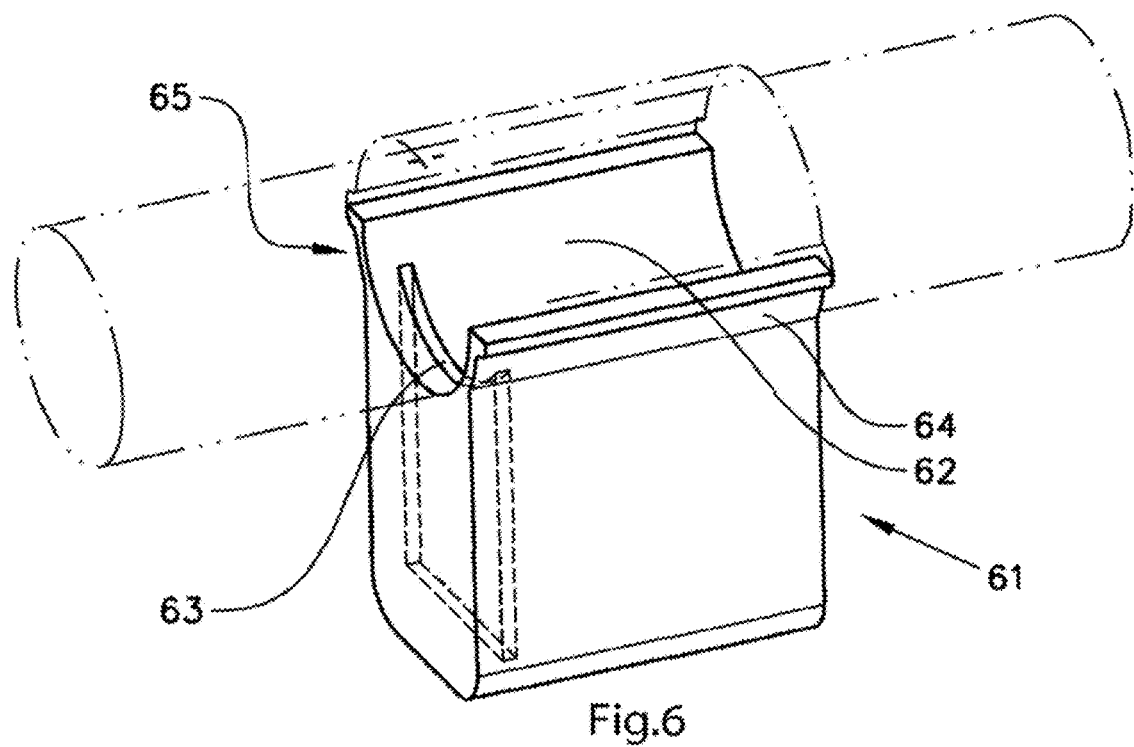
FIGS. 6-7 show views of the embodiments of FIGS. 5a and 5b.

The flat plate 51 is arranged in or adjacent to a casing 61, which is shown in a perspective view in FIG. 6. As can be seen in FIG. 6, in one embodiment, an outer wall 62 of the casing 61 is concavely curved so that it will essentially coincide with the outer shape of a blood vessel against which the casing 61 will be arranged. The curved outer wall 62 also comprises an opening 63 for the plate 51, through which opening the plate can move in its movements, In this embodiment, the tolerance between the dimensions of the opening and the plate should be such that the movements of the plate 51 are enabled, but also such that leakage of blood between the plate 51 and the opening 63 is essentially eliminated.

In one embodiment, also shown in FIG. 6, in order to make it possible to attach the valve 50 securely to a blood vessel, the casing 61 also comprises at least a first curved protruding part 64 for surrounding at least part of the circumference of a blood vessel. In another embodiment, the casing 61 also comprises a second curved protruding part 65 for surrounding at least part of the circumference of a blood vessel, so that the two parts 64, 65 may be arranged on opposite sides of a blood vessel to which the valve 50 is to be attached.

Figure 7:
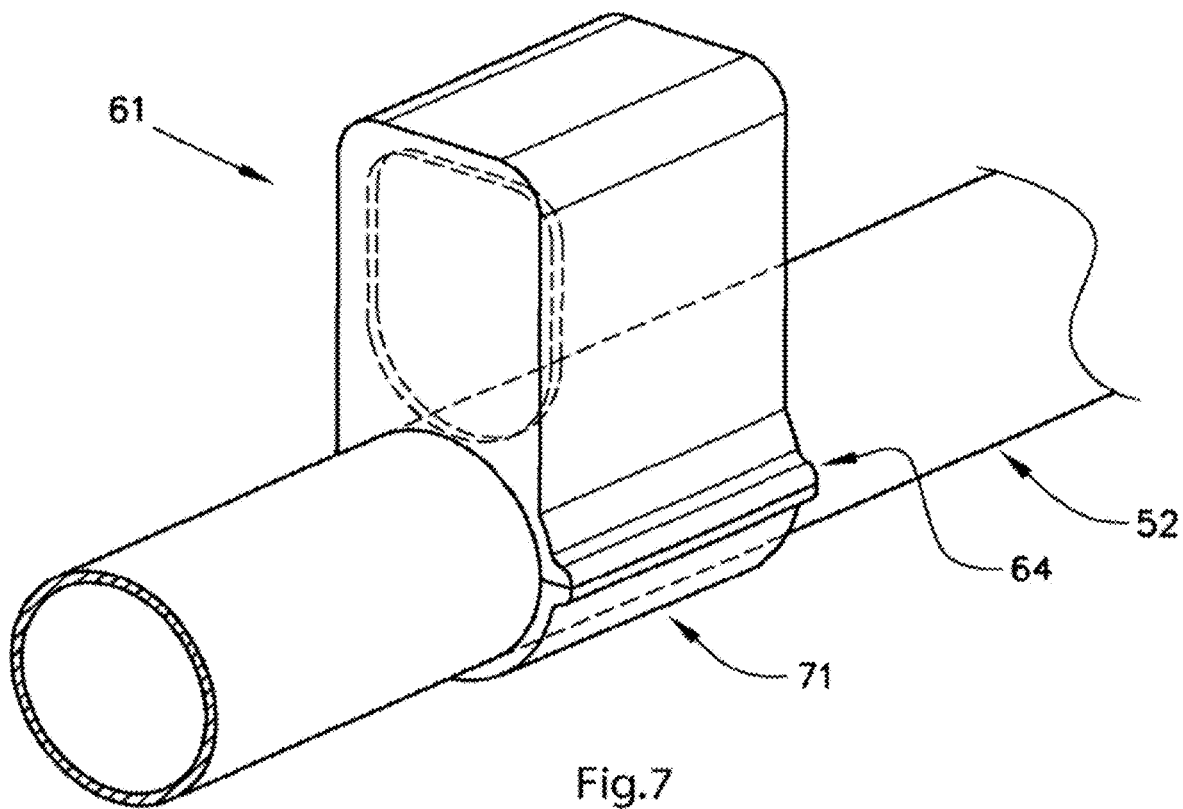

In some patients or in some positions in a patient's body, it may be possible to attach the valve 50 to a blood vessel 52 by means of letting the casing 61 of the valve surround the blood vessel entirely, which is shown in FIG. 7. For such applications, the valve can be made to also comprise a detachable part 71 for attachment to the casing 61 or to one or more of the protruding parts 64, 65. The valve may then be made to completely surround a blood vessel by means of at least one protruding part and said detachable part and/or by means of a curved outer wall of the valve, as shown in FIG. 7.

In the embodiments with the flat plate 51, the plate will thus in its closing movements move into (and out from, in an opening movement) a position in a blood vessel. In one embodiment, show in a side view in FIGS. 8a and 8b, in order to guide the plate 51 in these movements, the casing 61 of the valve also comprises a protruding guide 81 for guiding the movements of the plate 51 in the blood vessel 52.

The guide 81 is thus intended for being arranged inside the blood vessel 81, and is for that reason essentially shaped to coincide with the outer form of the plate, with a certain tolerance to enable the plate to move in the guide.

The guide 81 can be seen as an outer rail for the plate 51, and can comprise grooves for the plate 51 to move in.

Figure 8A:
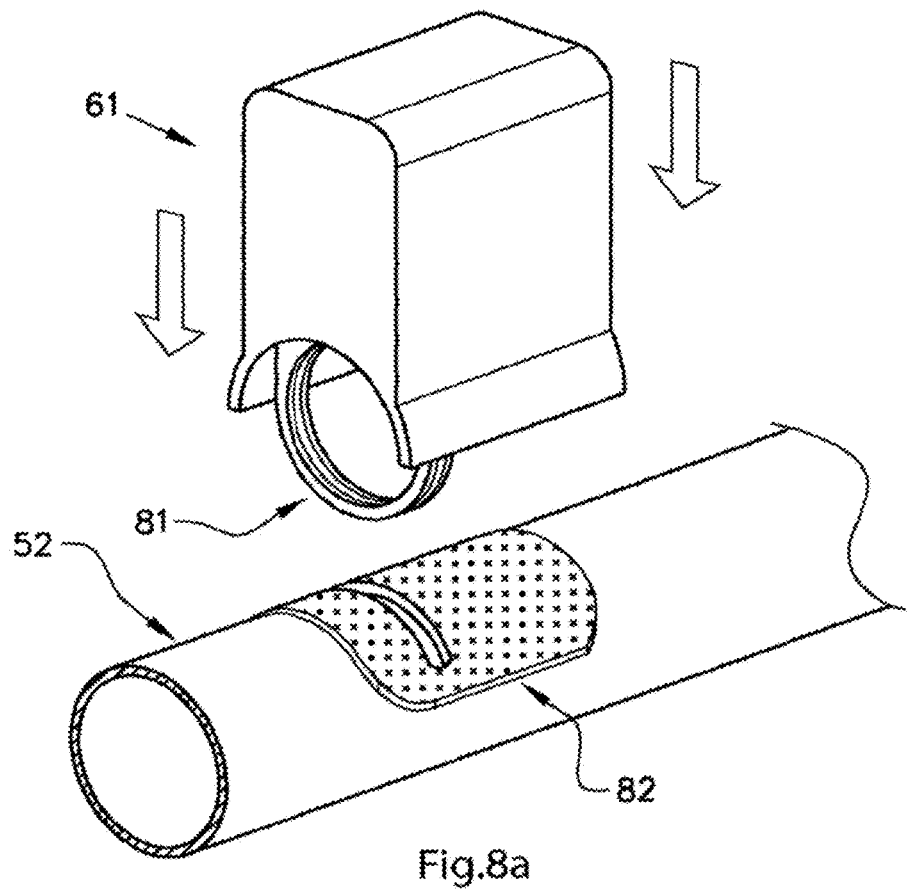
FIGS. 8a and 8b show views of the embodiments of FIGS. 5a and 5b.
Figure 8B:
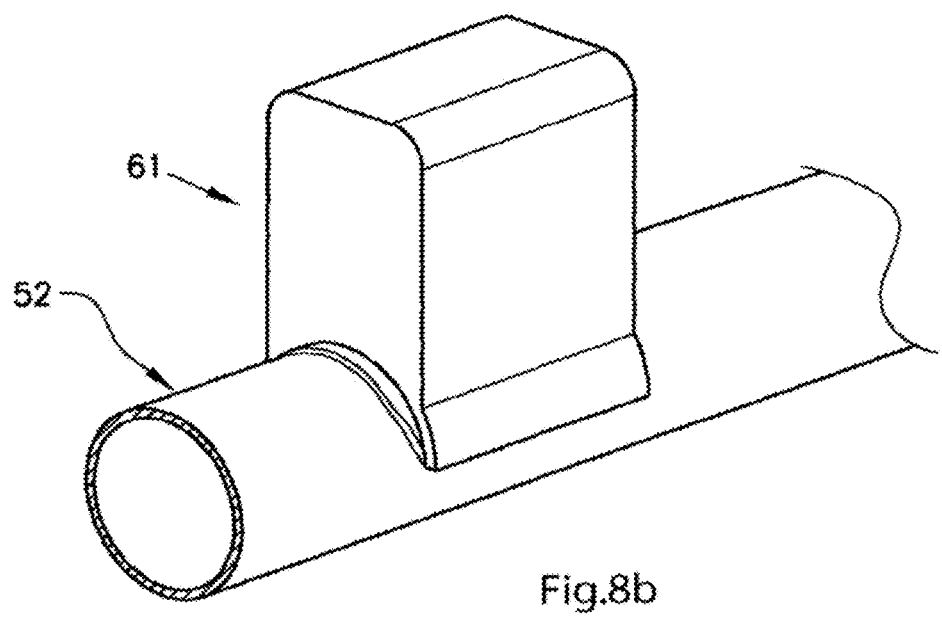

FIG. 8a also shows a vascular graft 82, by means of which the valve may be attached to the blood vessel 52.

Figure 9:
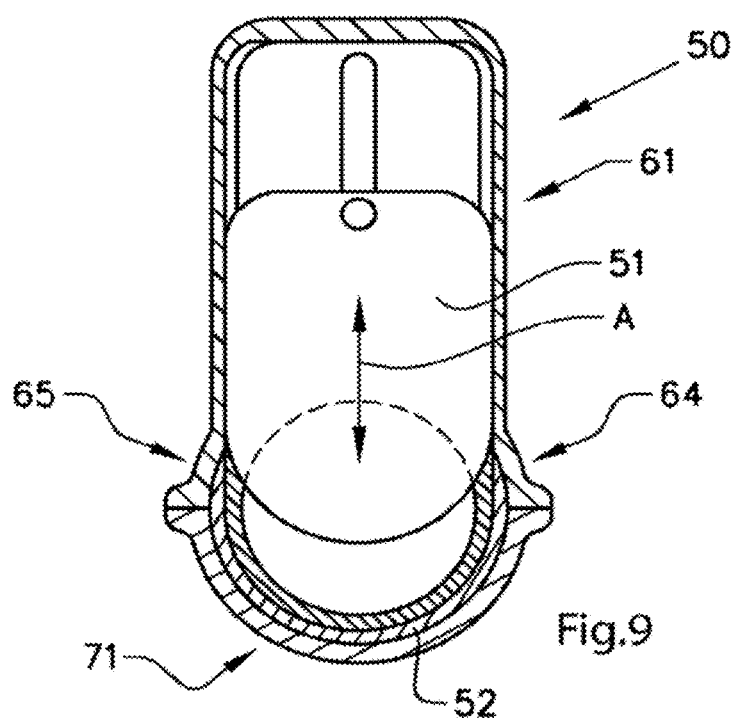
FIG. 9 shows a view of the embodiments of FIGS. 5a and 5b.

FIG. 9 shows a cross sectional view of a blood vessel 52, adjacent to which a valve 50 of the "flat plate" embodiment has been arranged, with protruding parts 64, 65, to which the detachable part 71 has been attached, so that the casing entirely surrounds the blood vessel 52. The flat plate 51 is also shown in FIG. 9, with its direction of movement being indicated by the arrow "A". As will be realized particularly well from FIG. 9, at least a portion of the moving part 51, i.e. a portion of the "flat plate", will in a non-closed position assume a position external to the blood vessel 52.

In some embodiments, the valve 50 will also preferably comprising a biasing mechanism for biasing the plate to an open position, so that the powered movement has to overcome a biasing force in order to perform the closing movement of the plate 51. Suitably, such a biasing mechanism comprises a spring mechanism. This is shown in FIG. 10, which shows an open side view of the valve 50 arranged adjacent to a blood vessel 52, and shows a possible spring mechanism 82 arranged in the casing 61.

Figure 10A:
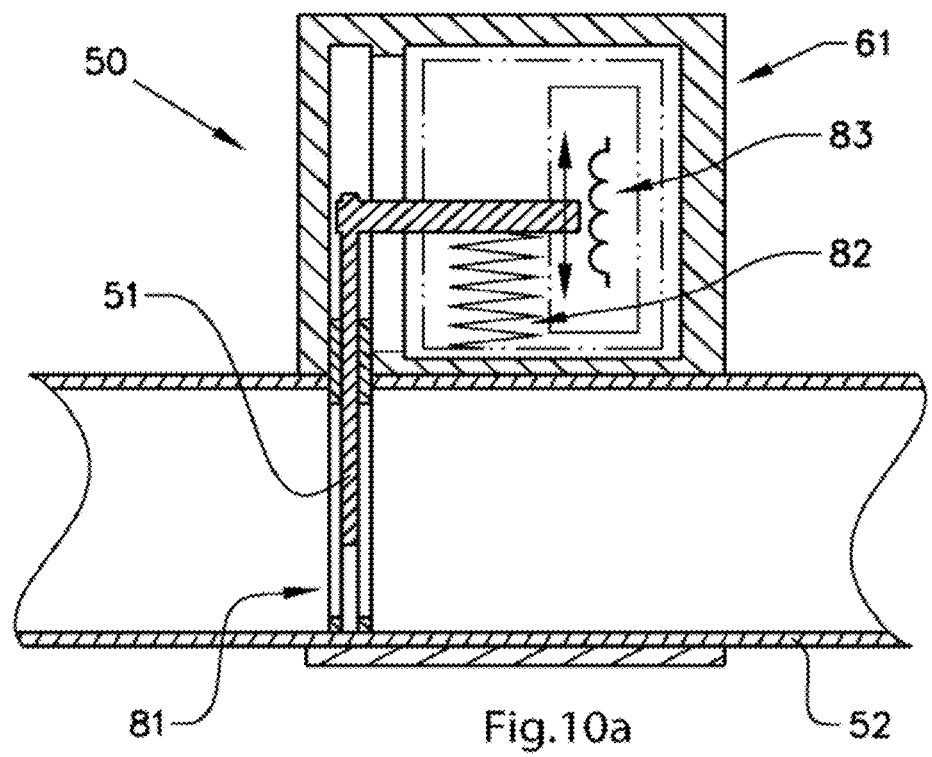
FIG. 10a-d show views of the embodiment of FIGS. 5a and 5b.

As can be seen in FIG. 10a, the spring mechanism cooperates with an abutment on the plate 51, in order to bias the plate 51 to an open position in the casing 61.

A suitable thickness for the plate 51 is 1 mm, although other thicknesses are also well within the scope of the present invention.

Figure 10B:
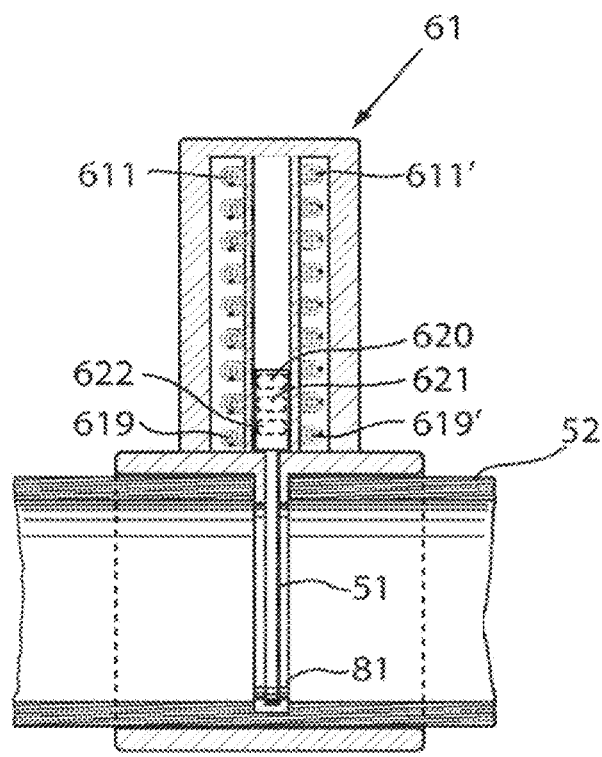
Figure 10C:
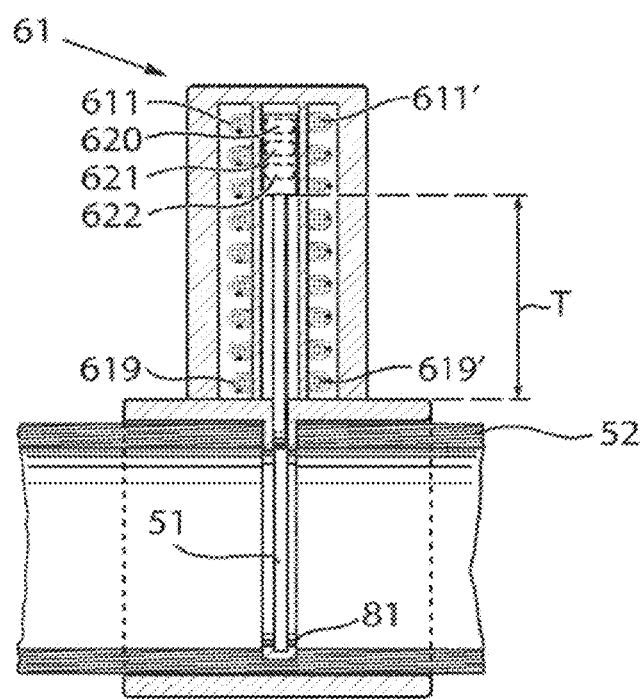
Figure 10D:
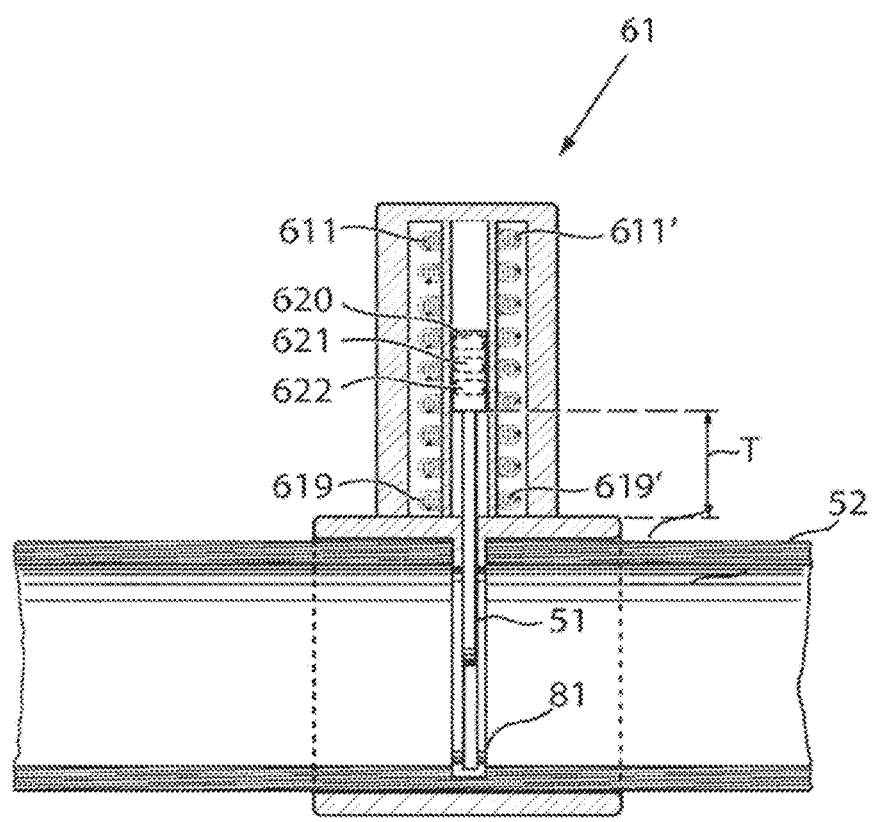

FIGS. 10b-10d show how the movements of the moving part 51 may be powered according to the invention, i.e. from an energy device external to the blood vessel. As shown, the casing 61, or to be more exact, the part or parts of the casing 61 which is arranged to house the moving part 51 outside of the blood vessel 52 is equipped with one or more coils 611-619, 611'-619', which are arranged to be energized by alternating current, AC, so as to interact with one or more magnets 620-622 magnets arranged on the moving part 51. The coils will thus in their interaction with the magnets cause the movement of the moving part 51.

The arrangement for running AC through the coils is not shown in the drawings nor described here, since such an arrangement lies within the scope of what a man skilled in the field has knowledge of.

As mentioned, the following embodiment can, in a non-exclusive manner, be envisioned for a closing mechanism which comprises one or more interacting magnets and coils:

the closing mechanism comprises at least two magnets, said closing mechanism being adapted to receive said additional pulses to affect a different magnet or a different group of magnets than said first pulse.

the closing mechanism comprises a coil which is adapted to be energized so as to cause said movement of the closing mechanism.

the closing mechanism comprises a coil which is adapted to be energized stepwise with two or more energy pulses so as to cause said movement of the closing mechanism.

the closing mechanism comprises a plurality of coils which are adapted to be energized stepwise so as to cause said movement of the closing mechanism.

Figure 48A:
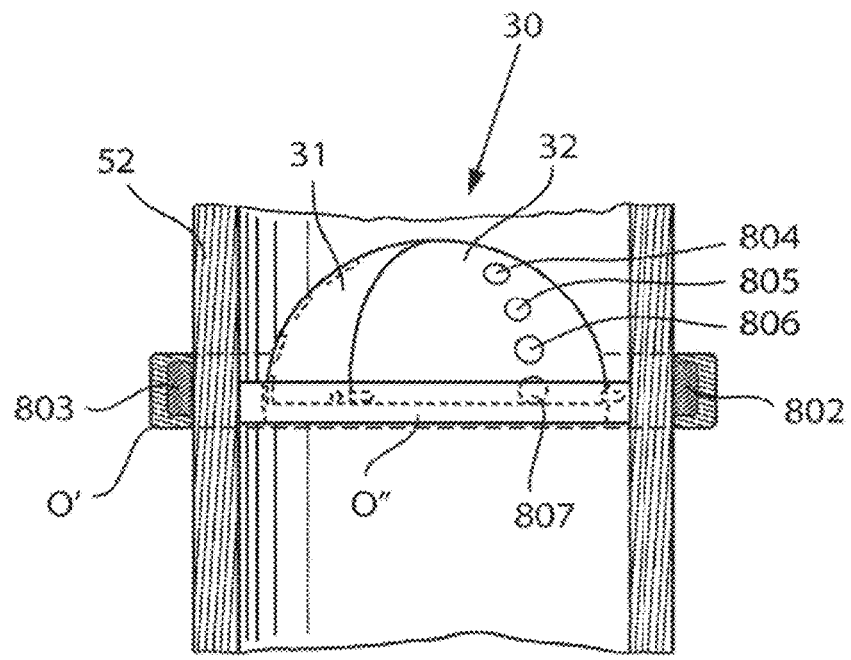
Figure 48B:
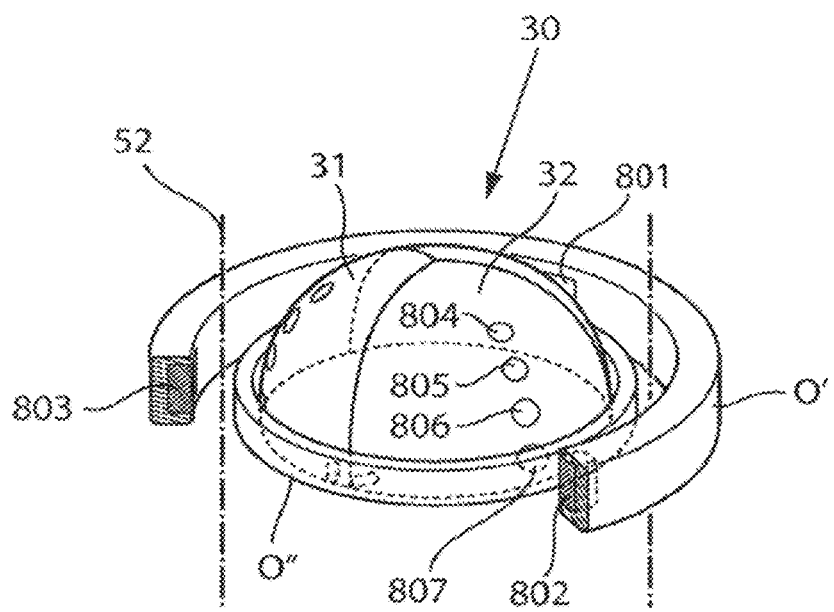
Figure 50:
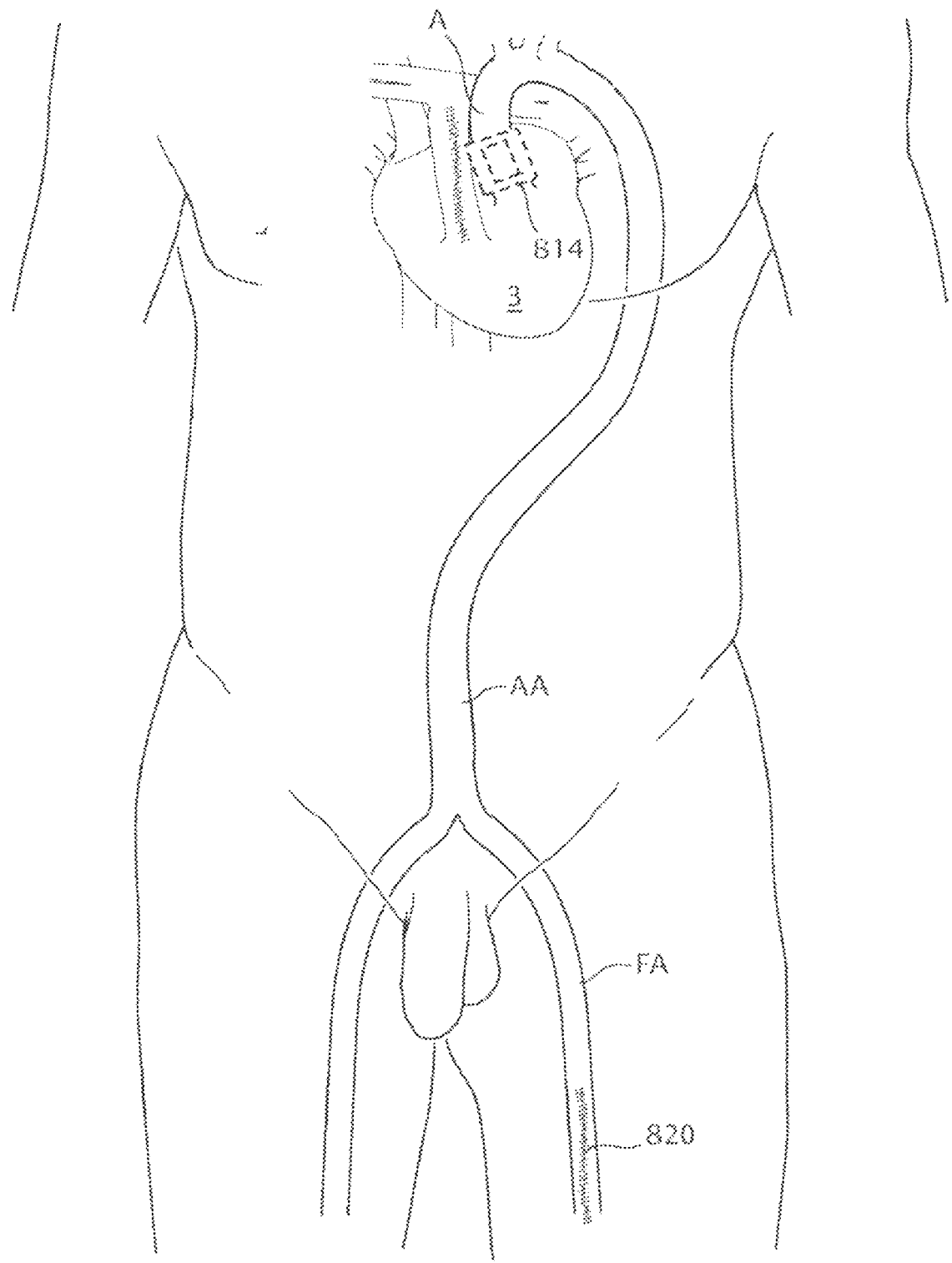
Figure 51:
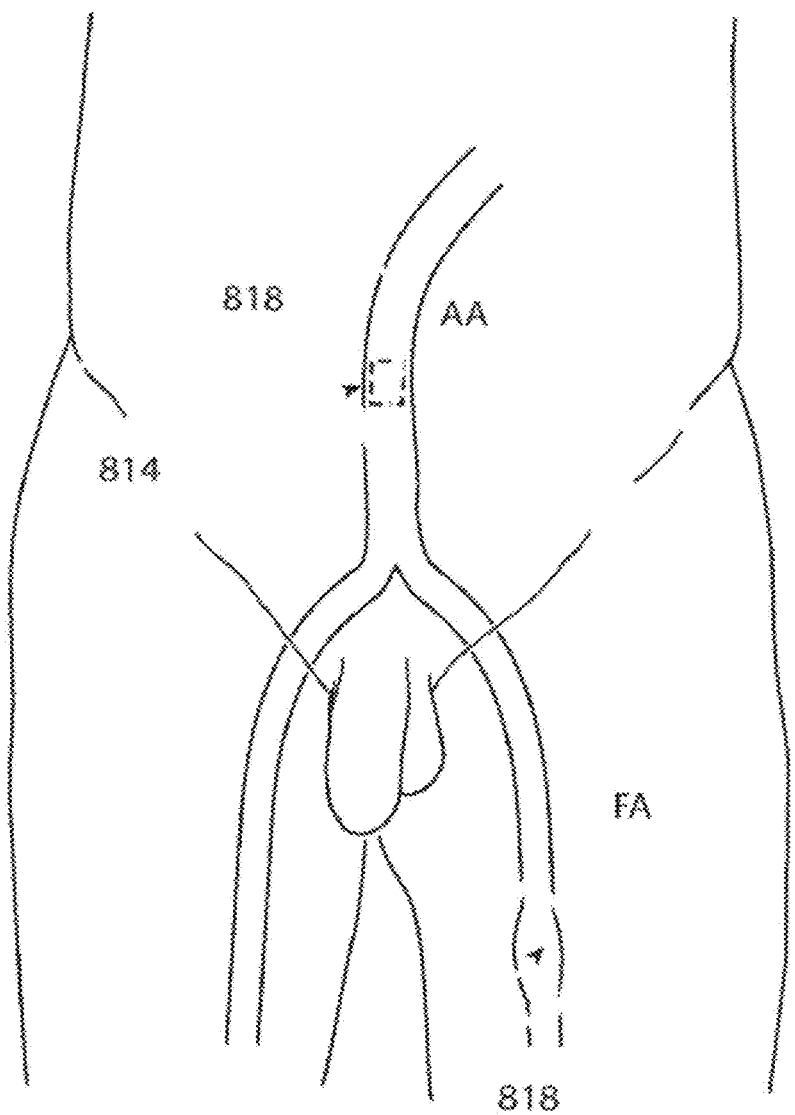
Figure 52:
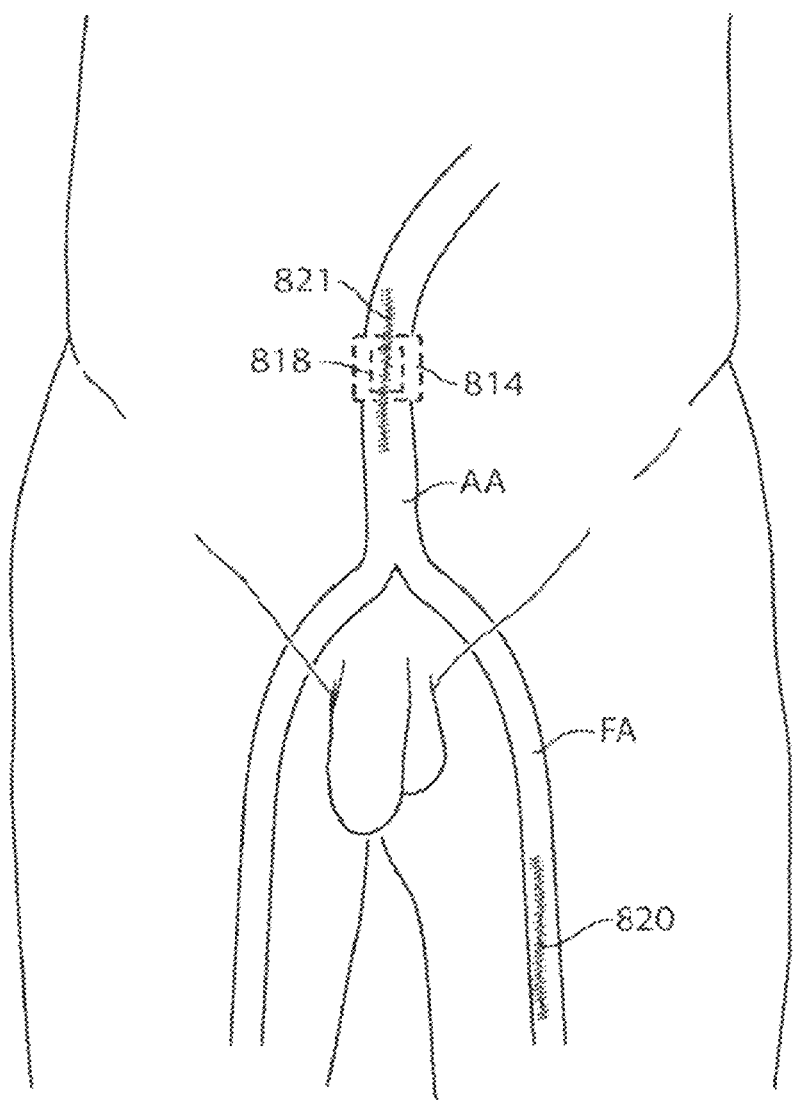

Regarding the "cupola embodiments" of the invention, their closing mechanism has been exemplified above in a number of ways, one of which is cooperating coils and magnets in various numbers and combinations. Those embodiments of the closing mechanism for the cupola embodiments which comprise one or more cooperating coils and magnets can also be arranged to be powered from an energy device which is arranged externally to the blood vessel, as exemplified by an embodiment shown in FIG. 48: A first part of the closing mechanism, in the example shown in FIG. 48 a ring O', is placed externally to the blood vessel 52. The coil or coils as described in the previous embodiments, here numbered 802, 803, is/are arranged on the ring O'.

The cupola embodiment, with the cupola parts 31, 32, 33 hinged about an inner casing part O", suitably also a ring, is then placed inside the blood vessel 52. The function of the interacting one or more coils and one or more magnets as described in the previous embodiments can then be performed in the manner described above, but now with an energy device in the form of the casing part O' with the coils arranged externally to the blood vessel 52.

Turning now to how and when the closing movements of the valve of the invention will take place, this will be described in the following, and will be shown using the drawings of the cupola embodiment 30 as an example. It should however be pointed out that the same principle may be used in other embodiments of the invention, such as for example, the "flat plate" embodiment 50.

As shown in FIGS. 3a and 3c, the valve may be made to also comprise a receiving device, shown as 38 in FIGS. 3a and 3c. Although the receiving device is shown in three parts in FIGS. 3a and 3c, the receiving device can naturally also comprise one or two parts, or more than three parts.

The receiving device or devices serve to receive a closing signal and for supplying this closing signal to the closing mechanism, which in turn is adapted to close upon the reception of the closing signal. The closing mechanism and the receiving device can be integrated into one unit, as shown throughout in the drawings, or they may be two separate units in the valve.

Figure 11A:
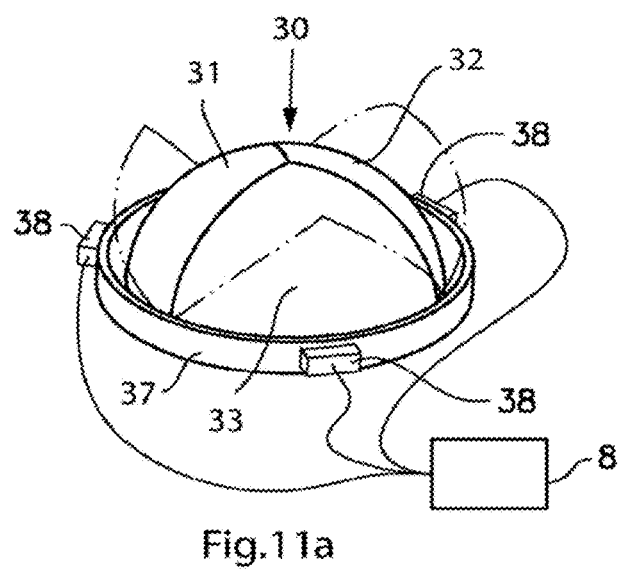
FIGS. 11a-b show various versions of the invention
Figure 11B:
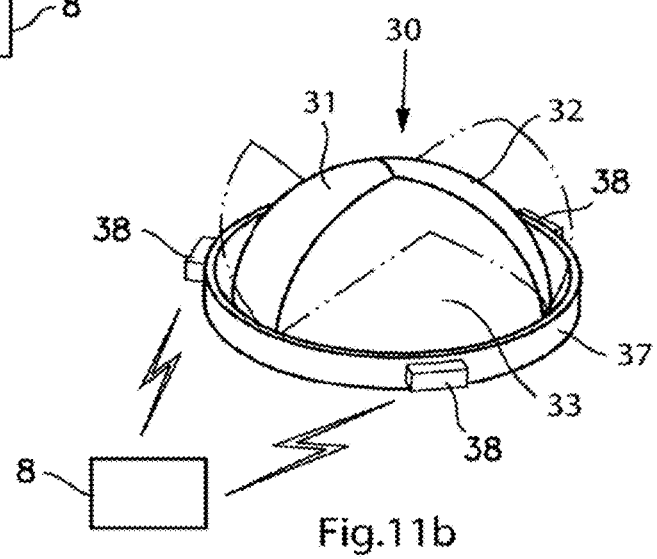

The exact design of the receiving device 38 can vary, but in a preferred embodiment, the receiving device is adapted to receive the opening and/or closing signal as an electrical signal. This is shown in FIGS. 11a and 11b, which also show, see FIG. 11a, that the signal may be received via cabling which is connected to the receiving device, or, FIG. 11b, that the signal may be received wirelessly, i.e. as radio signals, so that the receiving device or devices comprise a wireless receiver. In the case of a wireless signal, the receiving device will also in some embodiments comprise a demodulator for demodulating a received wireless signal.

Turning now to more details of how the moving parts of the closing mechanism of the various embodiments are made to perform their closing movements, this can be achieved in a large number of ways within the scope of the present invention, as will be obvious to those skilled in the field.

Figure 12:
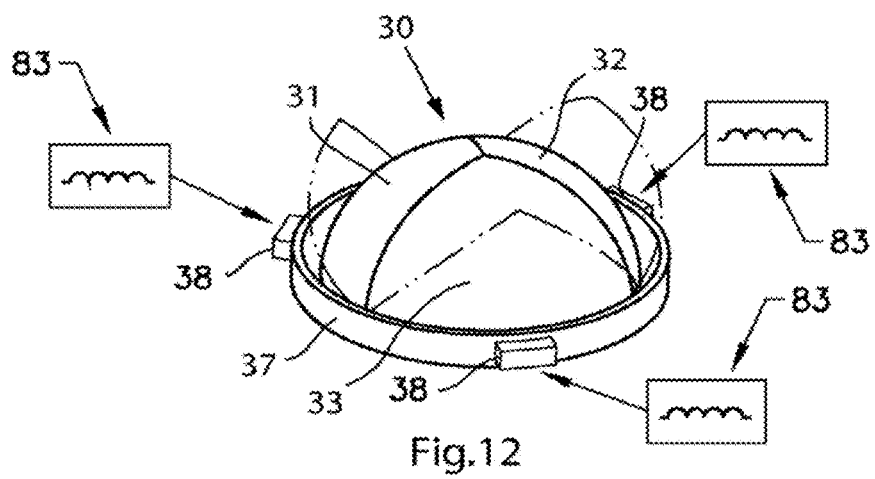
FIGS. 12-15 show various versions of the invention.

However, as shown in FIG. 12, in one embodiment, the closing mechanism may comprise one or more magnets, each of which interacts with a coil 83 in order to create movement of the moving parts 31, 32, and 33. As indicated in FIG. 12, each of the coils is arranged on the casing 37 at a central position for each moving part 31, 32, 33, with each of the interacting magnets being arranged at a position on a moving part which is immediately adjacent to the position of a coil. In the plate embodiment 50, the magnet is instead preferably placed on the plate, and the coil is housed inside the casing. The coil 83 is also shown in the plate embodiment in FIG. 10.

In the "spring and coil" embodiment of the closing mechanism, the motion of the moving parts is caused by passing an AC current through the coils.

In another embodiment, the closing mechanism comprises a mechanical element which is involved in the closing movements. A suitable example of such a mechanical element is a rotatable shaft, which may, for example, in the case of the "cupola embodiment" 20, 30, be arranged to interact with the hinges of the moving parts to cause the moving parts to open and/or to close.

In the "plate embodiment" 50, the rotatable shaft will instead be arranged inside the housing, and, for example, interacts with the plate by means of cogs.

Suitably, if a shaft is used, the rotatable shaft is attached to an engine which rotates the shaft, with the rotation of the shaft being controlled by the signals received by the receiving device.

Figure 13:
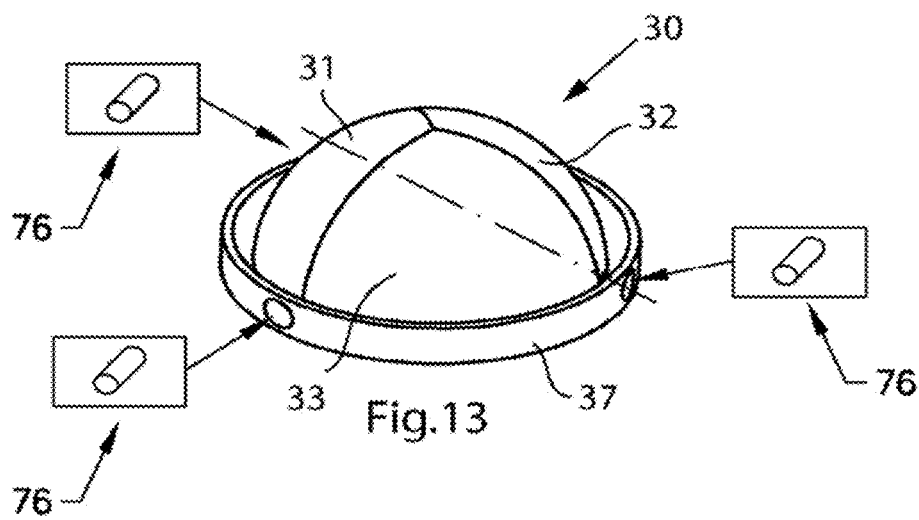

An example of the shaft embodiment is shown in FIG. 13, in which a symbolic shaft 76 is shown next to each of the hinge positions of the moving parts of the cupola. The engine which drives the shafts is not shown in FIG. 13.

Turning now to the signals which the receiving device of the valve is adapted to receive, these signals will in some embodiments be received from a source such as a sensor or some other device which is external to the valve, with said source however being connected to the receiving device, for example by means of cabling or wirelessly, as described above. Such a sensor is shown in FIGS. 11a and 11b with the reference number 88.

The signals which the receiving device is adapted to receive from this external source may be based upon a variety of parameters, some examples of which will be given below. It should be understood that these signals may also be combined, so that the receiving device receives input from more than one source or from more than one measurement:

In one embodiment, the receiving device of the valve is adapted to receive input signals which are the result of the blood pressure or blood flow at a defined point in the circulatory system of the user of the valve reaching a predetermined threshold, which thus indicates that a closing movement should be carried out by the valve.

In one embodiment, the receiving device of the valve is adapted to receive inputs signals as the result of a parameter which is related to the contraction of a muscle at a defined point in the user of the valve reaching a predetermined threshold. For example, this may be a measurement of the heart's phases, so that the valve is made to close at predefined points of the systolic and/or diastolic phases of the heart.

In general, with regard to the valve operating in conjunction with the heart in a predefined manner, the input signals to the receiving device may be received as the result of one or more predefined body generated parameters which is/are related to the contraction of the heart muscle reaching a predetermined threshold. Examples of such parameters are those mentioned, such as blood pressure, heart contractions (for example movement or bending or volume) and heart anti-contractions, and also heart electrical body generated signals.

In one embodiment, the artificial valve of the invention is adapted to cooperate with another device used by the mammal in question. Thus, in such an embodiment, the receiving device is adapted to receive the input signals as the result of a device generated signal, suitably related to the contraction of the heart. An example of such a device may be a so called pacemaker, and in this case, the input signals would be signals which indicate that the mammal's heart has reached a certain phase at which the artificial valve should close. The pacemaker will then serve the role of the device 8 of FIGS. 11a and 11b.

Figure 14:
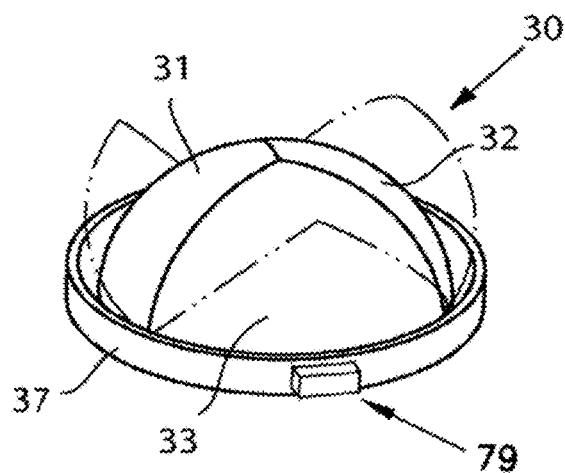

Thus, the receiving device can be adapted to receive said signal as the result of a certain threshold value being reached by a physical parameter of the mammal or a functional parameter of a device, As described above, the valve may be designed to cooperate with an external device such as a sensor or a device used by the user, such as a pacemaker. However, in alternative embodiments, as a complement or replacement to external sensors and devices, the valve will in itself comprise a sensor for sensing one or more parameters, such as a physical parameter of the mammal or a functional parameter of another device, such as, for example, the parameters enumerated above; such a sensor will then also generate input signals to the receiving device of the valve. This embodiment is shown in FIG. 14, in which the sensor 79 is shown as being arranged on the casing of the valve.

In one embodiment, the valve in addition comprises a control device for controlling the opening and closing of the valve, i.e. the movement of the moving parts of the valve. In this embodiment, the control device receives the input signals instead of or via the receiving device, processes the signals, and controls the operation of the valve accordingly.

Figure 15:
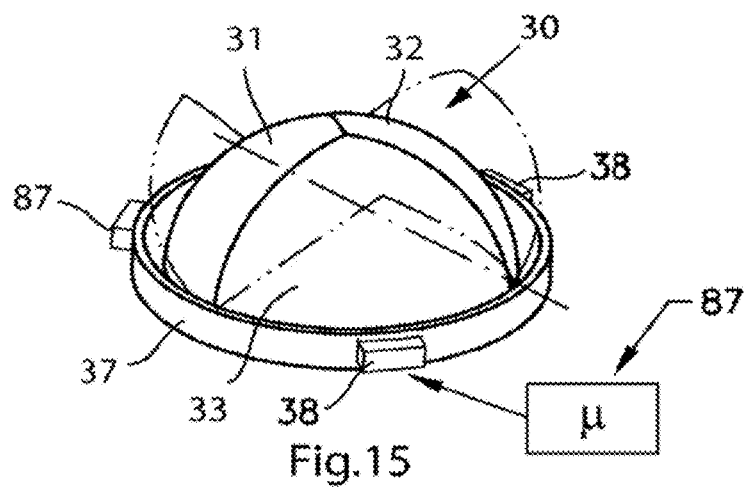
Figure 17A:
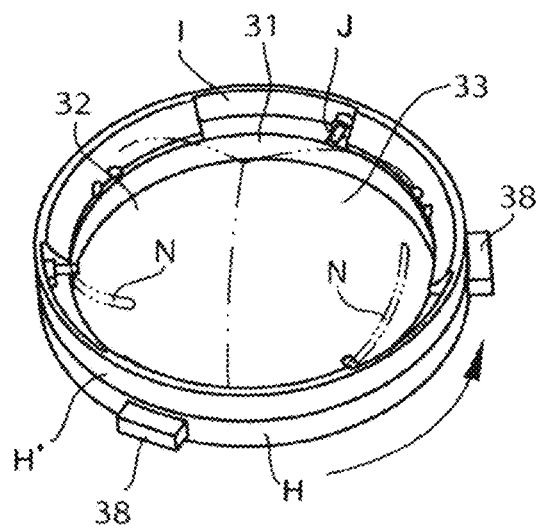
FIGS. 17a-d show versions of a powered movement.
Figure 17B:
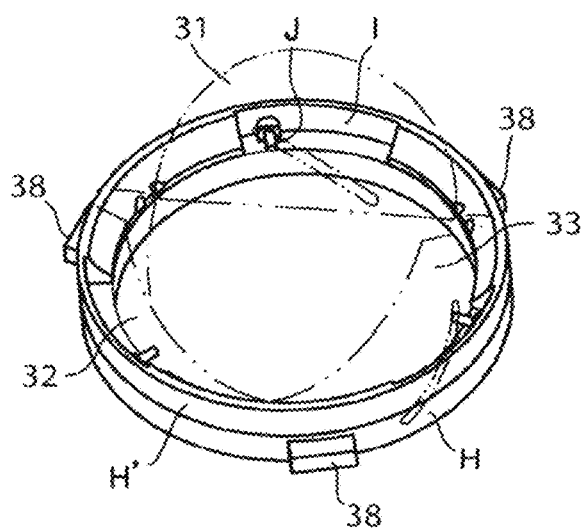
Figure 17C:
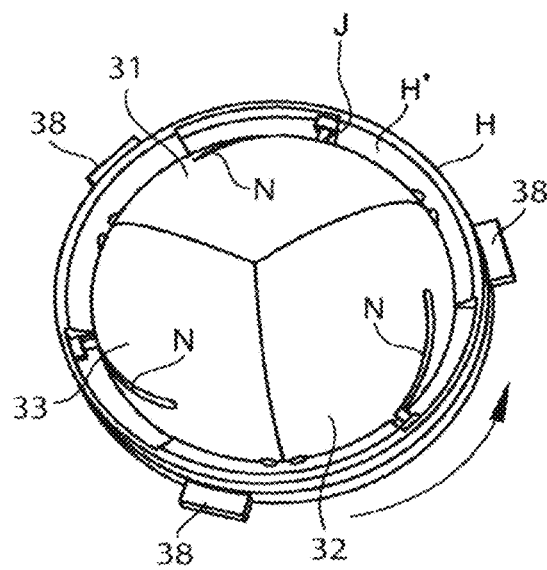
Figure 17D:
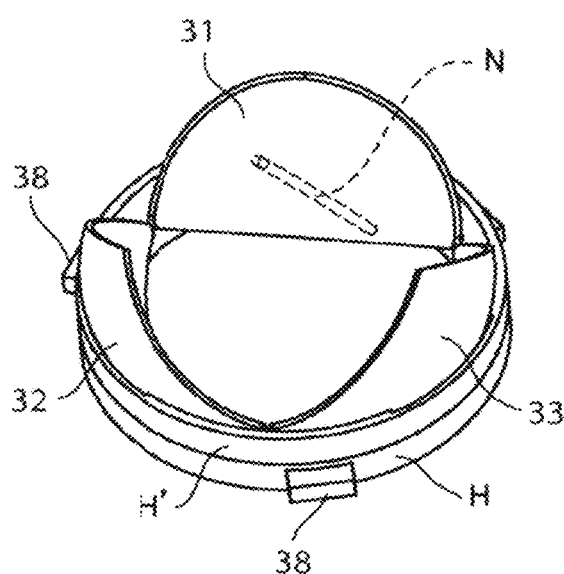

As indicated in FIG. 15, such a control device 87 suitably comprises a processor of some kind, for example a microprocessor, as well as a memory for storing executable code, and possibly also for storing parameters which are relevant to the operation of the valve, e.g. threshold parameters such as those mentioned above, and others.

Suitably, the control device controls the operating mechanism using input parameters which are received via the receiving device and/or sensed by an internal sensor.

As mentioned previously, the operating mechanism of the valve will in one embodiment comprise at least one magnet and at least one coil which interact with each other in order to cause an opening and/or closing movement of at least one of the moving parts of the valve.

In an alternative embodiment, as a complement or alternative to the spring/coil mechanism, the operating mechanism is attached to the casing, in the "cupola embodiments", or housed in the casing, in the case of the "plate embodiment", and comprises at least two parts, with a first part being adapted to move in relation to a second part to cause an opening or closing movement of said moving parts. In one embodiment, the first part is then the rotating shaft mentioned previously, which in the case of the "cupola embodiments" is adapted to rotate perpendicularly along the periphery of the blood vessel in which the valve may be implanted.

Regarding the choice of material for the parts of the valve, the moving parts are suitably made of titanium, but any suitable material could be used; the casing may preferably be manufactured in a ceramic material, but for example stainless steel or plastic materials can also be used. The hinges may be manufactured in titanium, stainless steel, plastic material or ceramics or any combination thereof.

In one embodiment, the moving parts of the valve are at least partially given a structured surface, i.e. a surface which has a pattern or a texture on it, since this has been found to facilitate the growth of mammal material upon a surface.

In one embodiment, the moving parts of the valve are at least partially covered by mammal valve material, such as that taken from a cow, a pig or a human being.

As shown in the drawings, the moving parts of the cupola, which can be two or more, are all essentially equally shaped, so that they represent essentially equal parts of the cupola. This is one embodiment, but embodiments in which the cupola is formed by unequally shaped parts are also within the scope of the present invention, as well as embodiments which use more than three moving parts to form a cupola.

The invention also discloses methods for implanting a valve of the invention into a mammal patient.

According to one embodiment of such a method, the following steps are carried out:
  inserting a needle or a tube-like instrument into the patient's thoraxial or abdominal or pelvic cavity,
  using the needle or tube-like instrument to fill a part of the patient's body with gas, thereby expanding said cavity,
  placing at least two laparoscopic trocars in said cavity,
  inserting a camera through one of the laparoscopic trocars into said cavity,
  inserting at least one dissecting tool through one of said at least two laparoscopic trocars,
  dissecting an area of a potential place for a valve of said blood vessel,
  placing a device of the invention in said blood vessel, and
  suturing in steps.

According to another embodiment of a method of the invention, the following steps are performed:
  cutting the skin of the mammal patient,
  dissecting an area of a blood vessel,
  placing said device in said blood vessel, and
  suturing in steps.

According to another embodiment of a method of the invention, the following steps are performed:
  inserting a needle or a tube-like instrument into the patient's thoraxial cavity,
  using the needle or tube-like instrument to fill a part of the patient's body with gas, thereby expanding said thoraxial cavity,
  placing at least two laparoscopic trocars in said cavity,
  inserting a camera through one of the laparoscopic trocars into said cavity,
  inserting at least one dissecting tool through one of said at least two laparoscopic trocars,
  dissecting an area of a heart valve,
  placing a device of the invention in said heart or connecting blood vessel, and
  suturing in steps.

According to another embodiment of a method of the invention, the following steps are performed:
  cutting the skin in the thoraxial wall of said mammal patient,
  dissecting an area of the artificial heart valve,
  placing the device of the invention in the heart or in a connecting blood vessel, and
  suturing in steps.

The method of the two embodiments described immediately above may also in one version include the following steps:
  dissecting a path for a cable into the right atrium of the heart
  cutting the skin and dissecting a subcutaneous place for a control unit, similar to a pacemaker position
  introducing the cable backwards from the right atrium of the heart to the position of the control unit following the venous blood vessels.

In this embodiment, the cable may also be made to reach vein subclavia or vein cephalica and to exit from that vessel.

The method of the invention may suitably include the step of placing a control unit in the subcutaneous area and connecting it to a cable for supplying the closing and/or opening signal to the valve.

In addition the method of the invention may comprise providing a power supply to wirelessly supply energy to the valve, in which case the dissection and placing includes the following steps:
  dissecting the area outside the heart valve
  placing a wireless control unit including said power supply to wirelessly supply the closing signal to said heart valve The invention also discloses a system for powering and controlling an artificial device or apparatus such as that disclosed by the invention.

In a preferred embodiment, the system comprises at least one switch implantable in the patient for manually and non-invasively controlling the apparatus In another preferred embodiment, the system comprises a wireless remote control for non-invasively controlling the apparatus.

In a preferred embodiment, the system comprises a hydraulic operation device for operating the apparatus.

In one embodiment, the system comprises comprising a motor or a pump for operating the apparatus.

FIG. 19 illustrates a system for treating a disease comprising an apparatus 10 of the present invention placed in the abdomen of a patient. An implanted energy-transforming device 302 is adapted to supply energy consuming components of the apparatus with energy via a power supply line 303. An external energy-transmission device 304 for non-invasively energizing the apparatus 10 transmits energy by at least one wireless energy signal. The implanted energy-transforming device 302 transforms energy from the wireless energy signal into electric energy which is supplied via the power supply line 303.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 304 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 302 is provided for transforming wireless energy of a first form transmitted by the energy-transmission device 304 into energy of a second form, which typically is different from the energy of the first form. The implanted apparatus 10 is operable in response to the energy of the second form. The energy-transforming device 302 may directly power the apparatus with the second form energy, as the energy-transforming device 302 transforms the first form energy transmitted by the energy-transmission device 304 into the second form energy. The system may further include an implantable accumulator, wherein the second form energy is used at least partly to charge the accumulator.

Alternatively, the wireless energy transmitted by the energy-transmission device 304 may be used to directly power the apparatus, as the wireless energy is being transmitted by the energy-transmission device 304. Where the system comprises an operation device for operating the apparatus, as will be described below, the wireless energy transmitted by the energy-transmission device 304 may be used to directly power the operation device to create kinetic energy for the operation of the apparatus.

The wireless energy of the first form may comprise sound waves and the energy-transforming device 302 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 304 also includes a wireless remote control having an external signal transmitter for transmitting a wireless control signal for non-invasively controlling the apparatus. The control signal is received by an implanted signal receiver which may be incorporated in the implanted energy-transforming device 302 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 20 illustrates the system of FIG. 19 in the form of a more generalized block diagram showing the apparatus 10, the energy-transforming device 302 powering the apparatus 100 via power supply line 303, and the external energy-transmission device 304, The patient's skin 305, generally shown by a vertical line, separates the interior of the patient to the right of the line from the exterior to the left of the line.

FIG. 21 shows an embodiment of the invention identical to that of FIG. 20, except that a reversing device in the form of an electric switch 306 operable for example by polarized energy also is implanted in the patient for reversing the apparatus 10. When the switch is operated by polarized energy the wireless remote control of the external energy-transmission device 304 transmits a wireless signal that carries polarized energy and the implanted energy-transforming device 302 transforms the wireless polarized energy into a polarized current for operating the electric switch 306. When the polarity of the current is shifted by the implanted energy-transforming device 302 the electric switch 1006 reverses the function performed by the apparatus 10.

FIG. 22 shows an embodiment of the invention identical to that of FIG. 20, except that an operation device 307 implanted in the patient for operating the apparatus 100 is provided between the implanted energy-transforming device 302 and the apparatus 10. This operation device can be in the form of a motor 307, such as an electric servomotor. The motor 307 is powered with energy from the implanted energy-transforming device 302, as the remote control of the external energy-transmission device 304 transmits a wireless signal to the receiver of the implanted energy-transforming device 302.

FIG. 23 shows an embodiment of the invention identical to that of FIG. 20, except that it also comprises an operation device is in the form of an assembly 308 including a motor/pump unit 309 and a fluid reservoir 310 is implanted in the patient. In this case the apparatus 10 is hydraulically operated, i.e. hydraulic fluid is pumped by the motor/pump unit 309 from the fluid reservoir 310 through a conduit 311 to the apparatus 10 to operate the apparatus, and hydraulic fluid is pumped by the motor/pump unit 309 back from the apparatus 10 to the fluid reservoir 310 to return the apparatus to a starting position. The implanted energy-transforming device 302 transforms wireless energy into a current, for example a polarized current, for powering the motor/pump unit 309 via an electric power supply line 312.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 302 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 24:
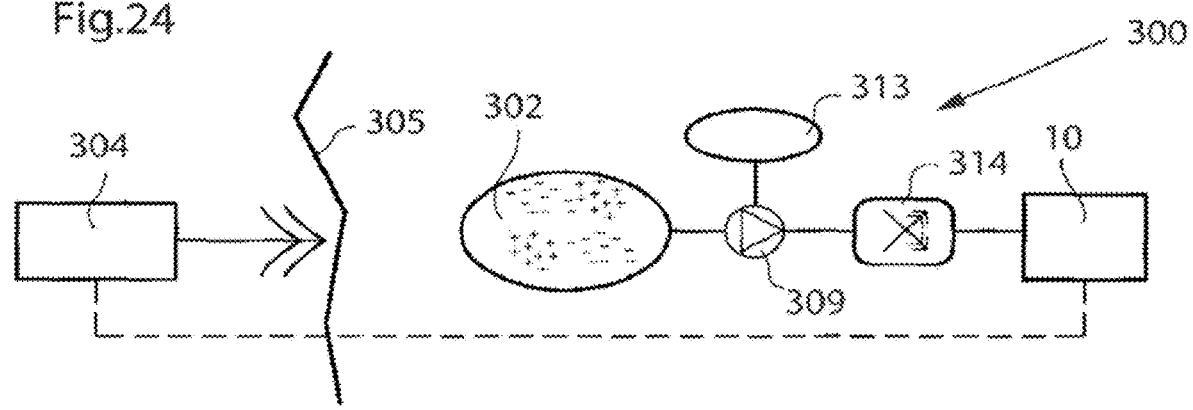

FIG. 24 shows an embodiment of the invention comprising the external energy-transmission device 304 with its wireless remote control, the apparatus 10, in this case hydraulically operated, and the implanted energy-transforming device 302, and further comprising a hydraulic fluid reservoir 313, a motor/pump unit 309 and an reversing device in the form of a hydraulic valve shifting device 314, all implanted in the patient. Of course the hydraulic operation could easily be performed by just changing the pumping direction and the hydraulic valve may therefore be omitted. The remote control may be a device separated from the external energy-transmission device or included in the same.

The motor of the motor/pump unit 309 is an electric motor. In response to a control signal from the wireless remote control of the external energy-transmission device 304, the implanted energy-transforming device 302 powers the motor/pump unit 309 with energy from the energy carried by the control signal, whereby the motor/pump unit 309 distributes hydraulic fluid between the hydraulic fluid reservoir 313 and the apparatus 10. The remote control of the external energy-transmission device 304 controls the hydraulic valve shifting device 314 to shift the hydraulic fluid flow direction between one direction in which the fluid is pumped by the motor/pump unit 309 from the hydraulic fluid reservoir 313 to the apparatus 10 to operate the apparatus, and another opposite direction in which the fluid is pumped by the motor/pump unit 309 back from the apparatus 10 to the hydraulic fluid reservoir 313 to return the apparatus to a starting position.

Figure 25:
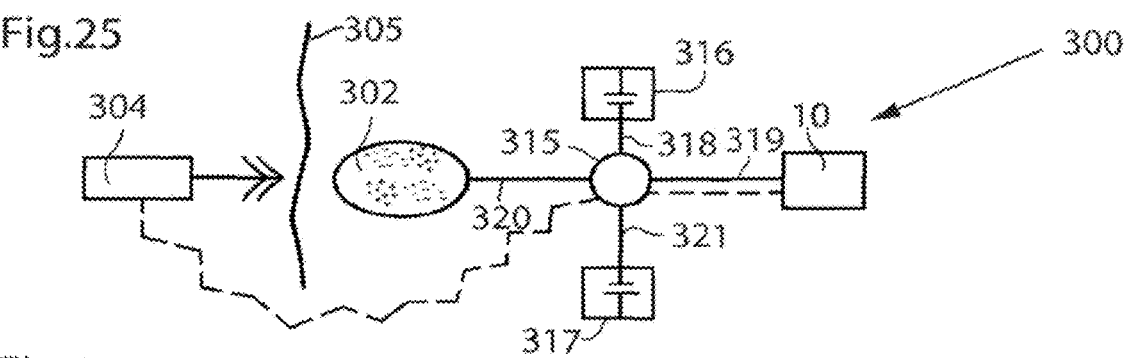

FIG. 25 shows an embodiment of the invention comprising the external energy-transmission device 304 with its wireless remote control, the apparatus 10, the implanted energy-transforming device 302, an implanted internal control unit 315 controlled by the wireless remote control of the external energy-transmission device 304, an implanted accumulator 316 and an implanted capacitor 317. The internal control unit 315 arranges storage of electric energy received from the implanted energy-transforming device 302 in the accumulator 316, which supplies energy to the apparatus 10. In response to a control signal from the wireless remote control of the external energy-transmission device 304, the internal control unit 315 either releases electric energy from the accumulator 316 and transfers the released energy via power lines 318 and 319, or directly transfers electric energy from the implanted energy-transforming device 302 via a power line 320, the capacitor 317, which stabilizes the electric current, a power line 321 and the power line 319, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

In accordance with an alternative, the capacitor 317 in the embodiment of FIG. 25 may be omitted. In accordance with another alternative, the accumulator 316 in this embodiment may be omitted.

Figure 26:
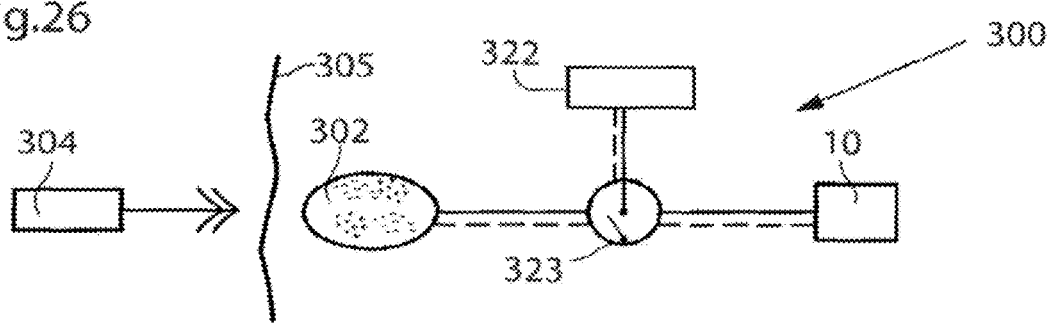

FIG. 26 shows an embodiment of the invention identical to that of FIG. 20, except that a battery 322 for supplying energy for the operation of the apparatus 10 and an electric switch 323 for switching the operation of the apparatus 10 also are implanted in the patient. The electric switch 323 may be controlled by the remote control and may also be operated by the energy supplied by the implanted energy-transforming device 302 to switch from an off mode, in which the battery 322 is not in use, to an on mode, in which the battery 322 supplies energy for the operation of the apparatus 10.

Figure 27:
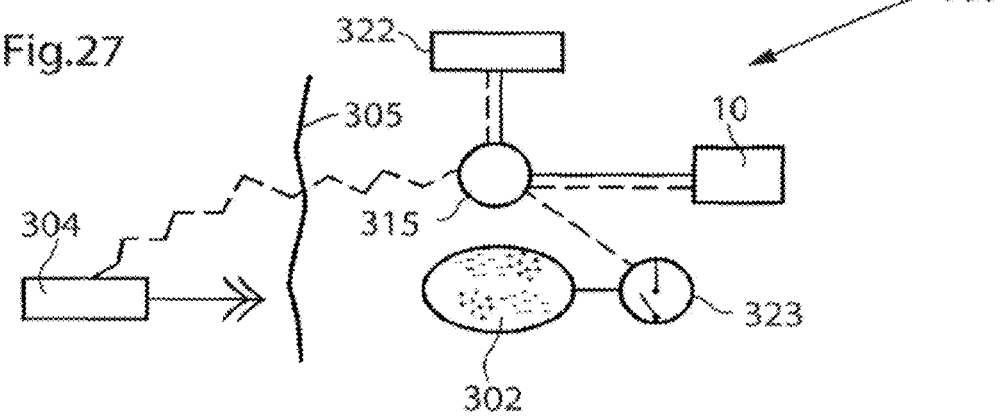

FIG. 27 shows an embodiment of the invention identical to that of FIG. 26, except that an internal control unit 315 controllable by the wireless remote control of the external energy-transmission device 304 also is implanted in the patient. In this case, the electric switch 323 is operated by the energy supplied by the implanted energy-transforming device 302 to switch from an off mode, in which the wireless remote control is prevented from controlling the internal control unit 315 and the battery is not in use, to a standby mode, in which the remote control is permitted to control the internal control unit 315 to release electric energy from the battery 322 for the operation of the apparatus 10.

Figure 28:
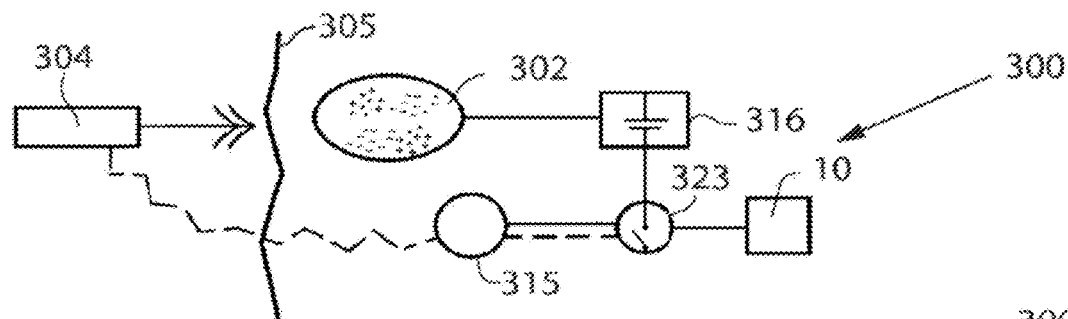

FIG. 28 shows an embodiment of the invention identical to that of FIG. 27, except that an accumulator 316 is substituted for the battery 322 and the implanted components are interconnected differently. In this case, the accumulator 316 stores energy from the implanted energy-transforming device 302. In response to a control signal from the wireless remote control of the external energy-transmission device 304, the internal control unit 315 controls the electric switch 323 to switch from an off mode, in which the accumulator 316 is not in use, to an on mode, in which the accumulator 316 supplies energy for the operation of the apparatus 10. The accumulator may be combined with or replaced by a capacitor.

Figure 29:
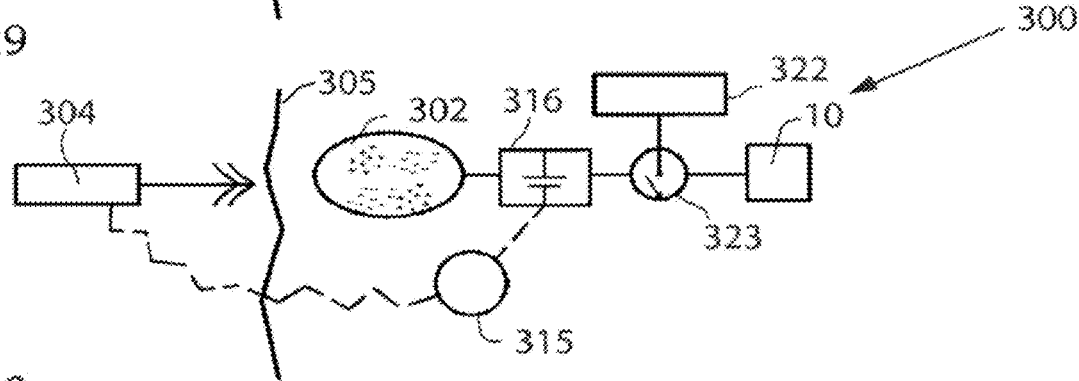

FIG. 29 shows an embodiment of the invention identical to that of FIG. 28, except that a battery 322 also is implanted in the patient and the implanted components are interconnected differently. In response to a control signal from the wireless remote control of the external energy-transmission device 304, the internal control unit 315 controls the accumulator 316 to deliver energy for operating the electric switch 323 to switch from an off mode, in which the battery 322 is not in use, to an on mode, in which the battery 322 supplies electric energy for the operation of the apparatus 10.

Alternatively, the electric switch 323 may be operated by energy supplied by the accumulator 316 to switch from an off mode, in which the wireless remote control is prevented from controlling the battery 322 to supply electric energy and is not in use, to a standby mode, in which the wireless remote control is permitted to control the battery 322 to supply electric energy for the operation of the apparatus 10.

It should be understood that the switch 323 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 30:
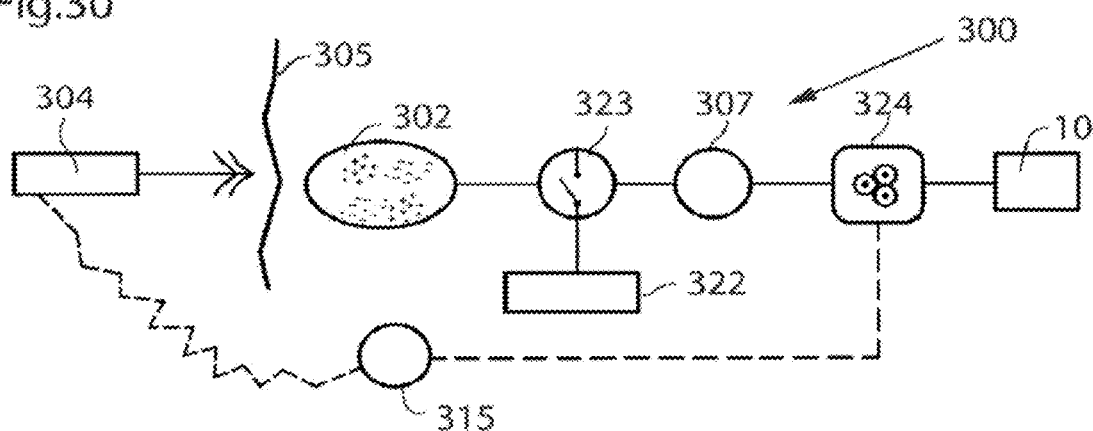

FIG. 30 shows an embodiment of the invention identical to that of FIG. 26, except that a motor 307, a mechanical reversing device in the form of a gear box 324, and an internal control unit 315 for controlling the gear box 324 also are implanted in the patient. The internal control unit 315 controls the gear box 324 to reverse the function performed by the apparatus 10 (mechanically operated). Even simpler is to switch the direction of the motor electronically. The gear box interpreted in its broadest embodiment may stand for a servo arrangement saving force for the operation device in favour of longer stroke to act.

Figure 31:
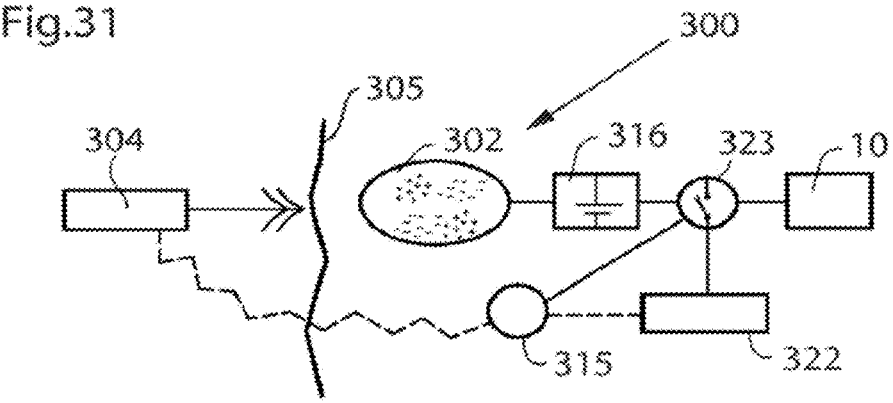

FIG. 31 shows an embodiment of the invention identical to that of FIG. 27 except that the implanted components are interconnected differently. Thus, in this case the internal control unit 315 is powered by the battery 322 when the accumulator 316, suitably a capacitor, activates the electric switch 323 to switch to an on mode. When the electric switch 323 is in its on mode the internal control unit 315 is permitted to control the battery 322 to supply, or not supply, energy for the operation of the apparatus 10.

Figure 32:
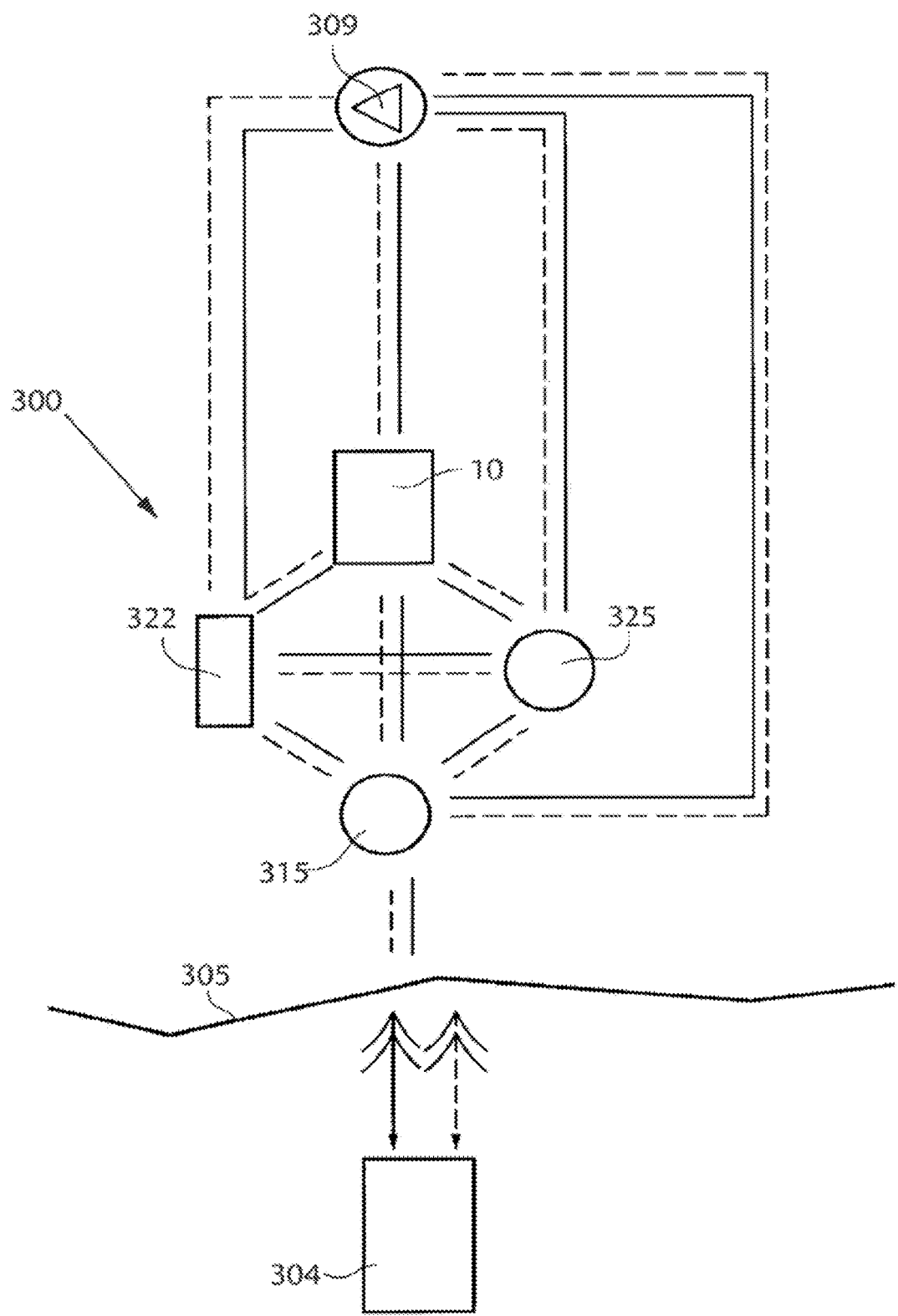

FIG. 32 schematically shows conceivable combinations of implanted components of the apparatus for achieving various communication options. Basically, there are the apparatus 10, the internal control unit 315, motor or pump unit 309, and the external energy-transmission device 304 including the external wireless remote control. As already described above the wireless remote control transmits a control signal which is received by the internal control unit 315, which in turn controls the various implanted components of the apparatus.

A feedback device, preferably comprising a sensor or measuring device 325, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 325 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 315, or alternatively the external wireless remote control of the external energy-transmission device 304, may control the apparatus 10 in response to signals from the sensor 325. A transceiver may be combined with the sensor 325 for sending information on the sensed physical parameter to the external wireless remote control. The wireless remote control may comprise a signal transmitter or transceiver and the internal control unit 315 may comprise a signal receiver or transceiver. Alternatively, the wireless remote control may comprise a signal receiver or transceiver and the internal control unit 315 may comprise a signal transmitter or transceiver. The above transceivers, transmitters and receivers may be used for sending information or data related to the apparatus 10 from inside the patient's body to the outside thereof.

Where the motor/pump unit 309 and battery 322 for powering the motor/pump unit 309 are implanted, information related to the charging of the battery 322 may be fed back. To be more precise, when charging a battery or accumulator with energy feed back information related to said charging process is sent and the energy supply is changed accordingly.

Figure 33:
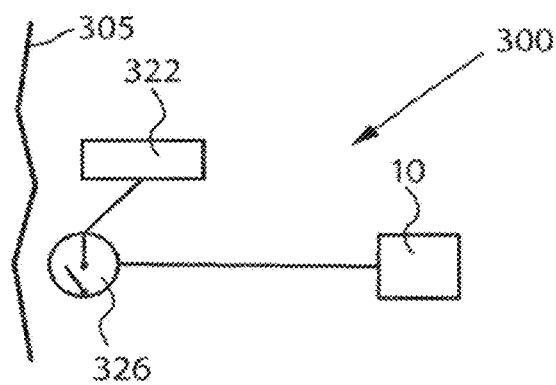

FIG. 33 shows an alternative embodiment wherein the apparatus 10 is regulated from outside the patient's body. The system 300 comprises a battery 322 connected to the apparatus 10 via a subcutaneous electric switch 326. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 34:
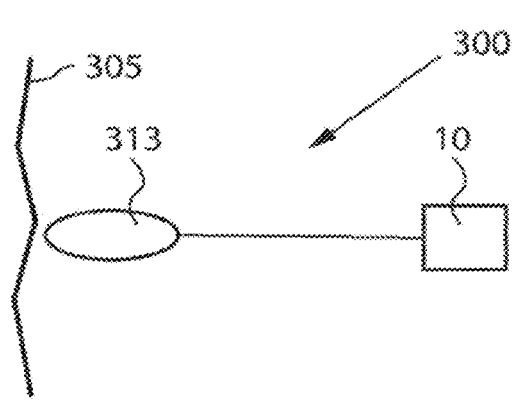

FIG. 34 shows an alternative embodiment, wherein the system 300 comprises a hydraulic fluid reservoir 313 hydraulically connected to the apparatus. Non-invasive regulation is performed by manually pressing the hydraulic reservoir connected to the apparatus.

The system may include an external data communicator and an implantable internal data communicator communicating with the external data communicator. The internal communicator feeds data related to the apparatus or the patient to the external data communicator and/or the external data communicator feeds data to the internal data communicator.

Figure 35:
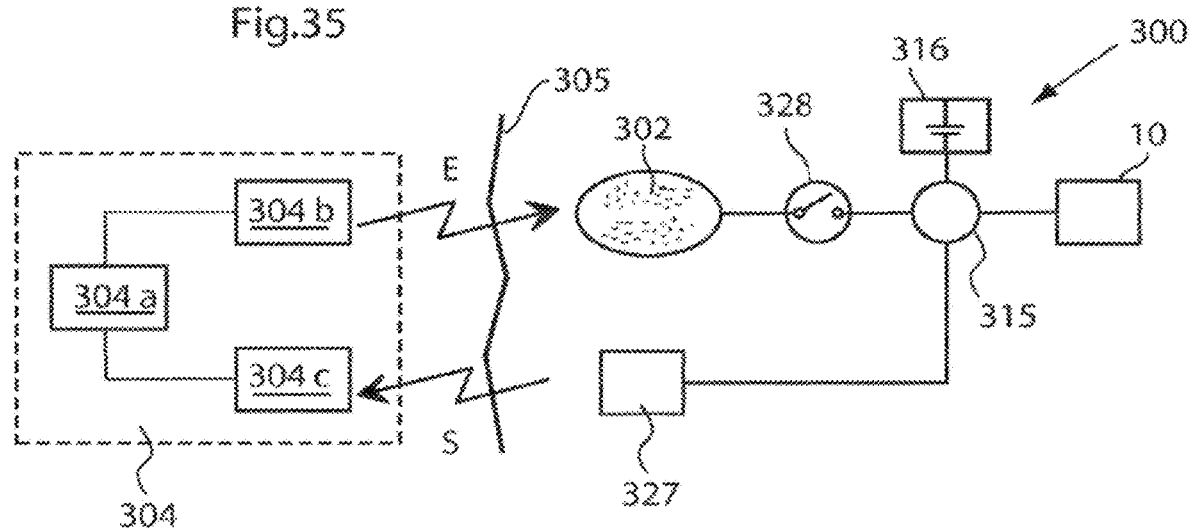
FIG. 35 is a schematic block diagram illustrating an arrangement for supplying an accurate amount of energy used for the operation of the apparatus shown in FIG. 19.

FIG. 35 schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 302 connected to implanted energy consuming components of the apparatus 10. Such an energy receiver 302 may include an energy source and/or an energy-transforming device. Briefly described, wireless energy is transmitted from an external energy source 304a located outside the patient and is received by the internal energy receiver 302 located inside the patient.

The internal energy receiver is adapted to directly or indirectly supply received energy to the energy consuming components of the apparatus 10 via a switch 326. An energy balance is determined between the energy received by the internal energy receiver 302 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 35 the patient's skin is indicated by a vertical line 305. Here, the energy receiver comprises an energy-transforming device 302 located inside the patient, preferably just beneath the patient's skin 305. Generally speaking, the implanted energy-transforming device 302 may be placed in the abdomen, thorax, muscle fascia (e.g. in the abdominal wall), subcutaneously, or at any other suitable location. The implanted energy-transforming device 302 is adapted to receive wireless energy E transmitted from the external energy-source 304a provided in an external energy-transmission device 304 located outside the patient's skin 305 in the vicinity of the implanted energy-transforming device 302.

As is well known in the art, the wireless energy E may generally be transferred by means of any suitable Transcutaneous Energy Transfer (TET) device, such as a device including a primary coil arranged in the external energy source 304a and an adjacent secondary coil arranged in the implanted energy-transforming device 302. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 304b that controls the external energy source 304a based on the determined energy balance to regulate the amount of transferred energy. In order to transfer the correct amount of energy, the energy balance and the required amount of energy is determined by means of a determination device including an implanted internal control unit 315 connected between the switch 326 and the apparatus 10.

The internal control unit 315 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 316 may optionally be connected to the implanted energy-transforming device 302 via the control unit 315 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 302, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 315 is further connected to an internal signal transmitter 327, arranged to transmit a control signal reflecting the determined required amount of energy, to an external signal receiver 304c connected to the external control unit 304b. The amount of energy transmitted from the external energy source 304a may then be regulated in response to the received control signal.

Alternatively, the determination device may include the external control unit 304b. In this alternative, sensor measurements can be transmitted directly to the external control unit 304b wherein the energy balance and/or the currently required amount of energy can be determined by the external control unit 304b, thus integrating the above-described function of the internal control unit 315 in the external control unit 304b. In that case, the internal control unit 315 can be omitted and the sensor measurements are supplied directly to the internal signal transmitter 327 which sends the measurements over to the external signal receiver 304c and the external control unit 304b. The energy balance and the currently required amount of energy can then be determined by the external control unit 304b based on those sensor measurements.

Hence, the present solution according to the arrangement of FIG. 35 employs the feedback of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 327 and the external signal receiver 304c may be implemented as separate units using suitable signal transfer means, such as radio, IR (Infrared) or ultrasonic signals. Alternatively, the internal signal transmitter 327 and the external signal receiver 304c may be integrated in the implanted energy-transforming device 302 and the external energy source 304a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 17, the switch 326 is either separate and controlled by the internal control unit 315, or integrated in the internal control unit 315. It should be understood that the switch 326 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 35 may operate basically in the following manner. The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b instead depending on the implementation, as mentioned above. In that case, the control signal may carry measurement results from various sensors. The amount of energy emitted from the external energy source 304a can then be regulated by the external control unit 304b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 304a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 36:
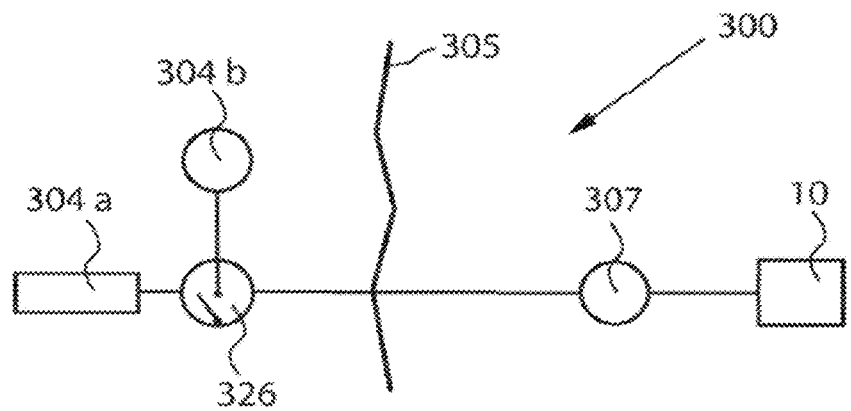
FIG. 36 schematically shows an embodiment of the system, in which the apparatus is operated with wire bound energy.

With reference to FIG. 36, although wireless transfer of energy for operating the apparatus has been described above to enable non-invasive operation, it will be appreciated that the apparatus can be operated with wire bound energy as well. Such an example is shown in FIG. 18, wherein an external switch 326 is interconnected between the external energy source 304a and an operation device, such as an electric motor 307 operating the apparatus 10. An external control unit 304b controls the operation of the external switch 326 to effect proper operation of the apparatus 10.

Figure 37:
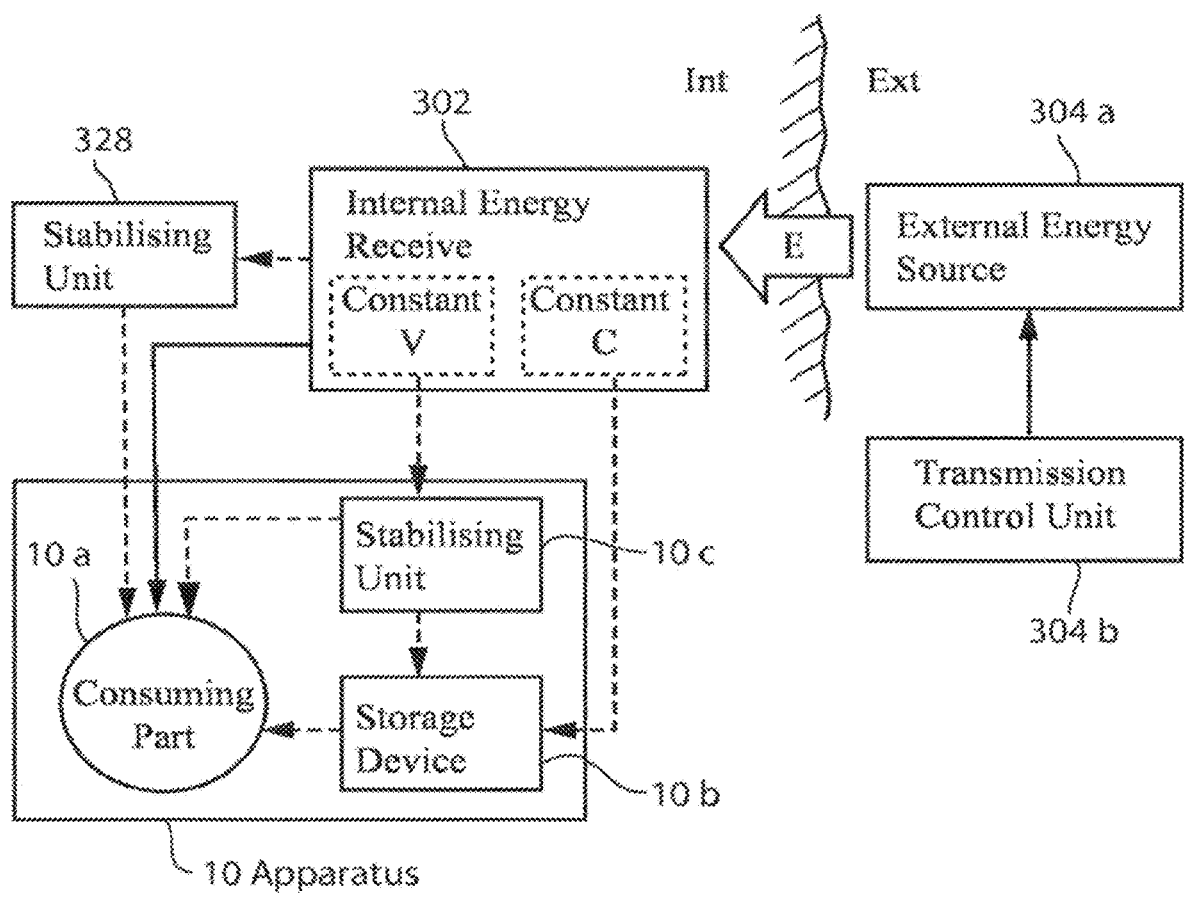
FIG. 37 is a more detailed block diagram of an arrangement for controlling the transmission of wireless energy used for the operation of the apparatus shown in FIG. 19.

FIG. 37 illustrates different embodiments for how received energy can be supplied to and used by the apparatus 10. Similar to the example of FIG. 17, an internal energy receiver 302 receives wireless energy E from an external energy source 304a which is controlled by a transmission control unit 304b. The internal energy receiver 302 may comprise a constant voltage circuit, indicated as a dashed box "constant V" in the figure, for supplying energy at constant voltage to the apparatus 10. The internal energy receiver 302 may further comprise a constant current circuit, indicated as a dashed box "constant C" in the figure, for supplying energy at constant current to the apparatus 10.

The apparatus 10 comprises an energy consuming part 10a, which may be a motor, pump, restriction device, or any other medical appliance that requires energy for its electrical operation. The apparatus 10 may further comprise an energy storage device 10b for storing energy supplied from the internal energy receiver 302. Thus, the supplied energy may be directly consumed by the energy consuming part 10a, or stored by the energy storage device 10b, or the supplied energy may be partly consumed and partly stored. The apparatus 10 may further comprise an energy stabilizing unit 10c for stabilizing the energy supplied from the internal energy receiver 302. Thus, the energy may be supplied in a fluctuating manner such that it may be necessary to stabilize the energy before consumed or stored.

The energy supplied from the internal energy receiver 302 may further be accumulated and/or stabilized by a separate energy stabilizing unit 328 located outside the apparatus 10, before being consumed and/or stored by the apparatus 10. Alternatively, the energy stabilizing unit 328 may be integrated in the internal energy receiver 302. In either case, the energy stabilizing unit 328 may comprise a constant voltage circuit and/or a constant current circuit.

It should be noted that FIG. 35 and FIG. 36 illustrate some possible but non-limiting implementation options regarding how the various shown functional components and elements can be arranged and connected to each other. However, the skilled person will readily appreciate that many variations and modifications can be made within the scope of the present invention.

Figure 38:
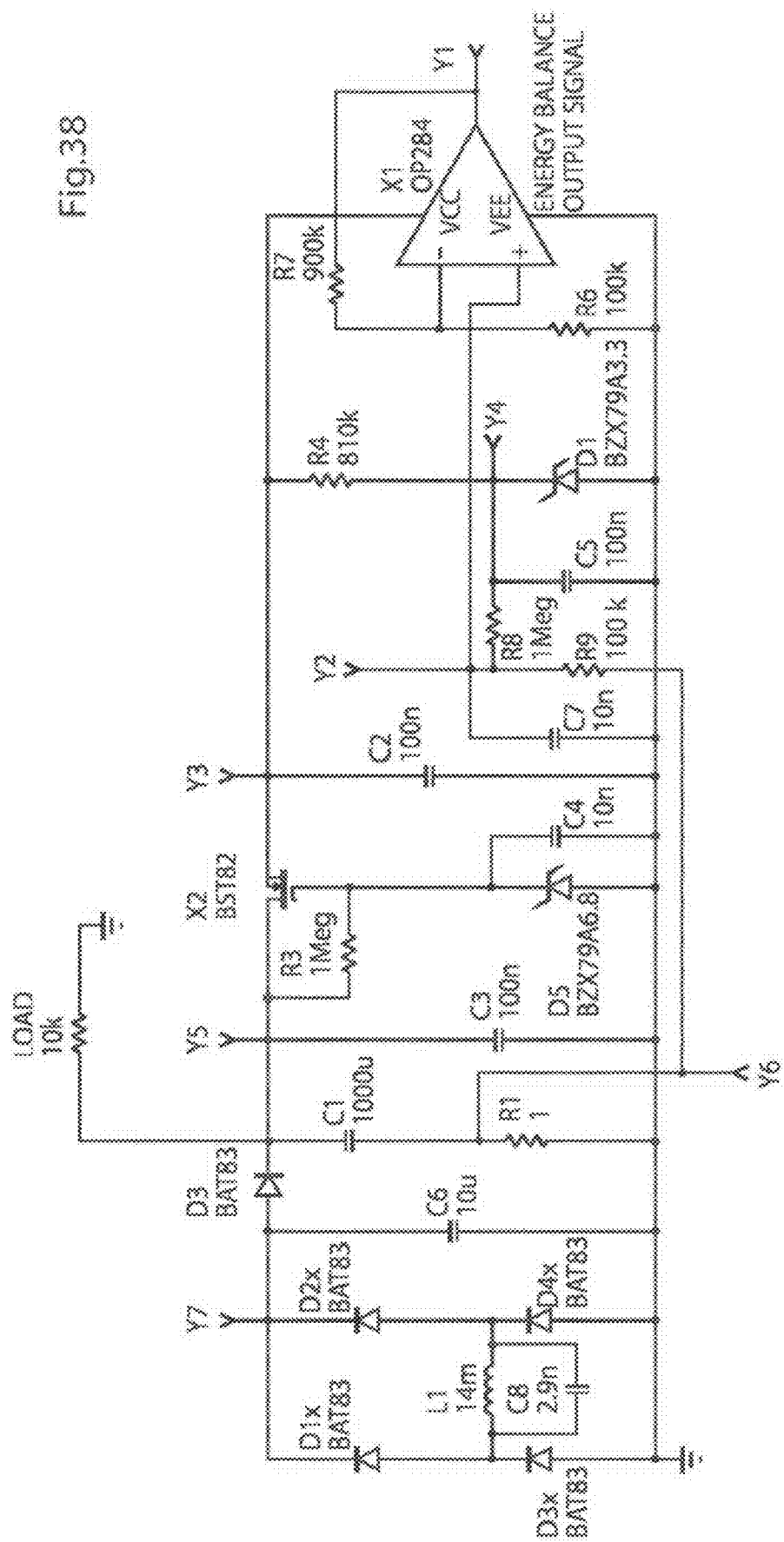
FIG. 38 is a circuit for the arrangement shown in FIG. 20, according to a possible implementation example.

FIG. 38 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 38 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 21; the transmitting parts of the system are excluded.

The implementation of the general concept of energy balance and the way the information is transmitted to the external energy transmitter can of course be implemented in numerous different ways. The schematic FIG. 38 and the above described method of evaluating and transmitting the information should only be regarded as examples of how to implement the control system.

CIRCUIT DETAILS

In FIG. 38 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 306 of FIG. 21 could be incorporated in any of the embodiments of FIGS. 24-30, the hydraulic valve shifting device 314 of FIG. 24 could be incorporated in the embodiment of FIG. 23, and the gear box 324 could be incorporated in the embodiment of FIG. 22. Please observe that the switch simply could mean any electronic circuit or component.

The embodiments described in connection with FIGS. 35, 37 and 38 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the system may comprise any of the following:

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming components of the apparatus, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the apparatus is consumed to operate the apparatus, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 39-42 show in more detail block diagrams of four different ways of hydraulically or pneumatically powering an implanted apparatus according to the invention.

Figure 39:
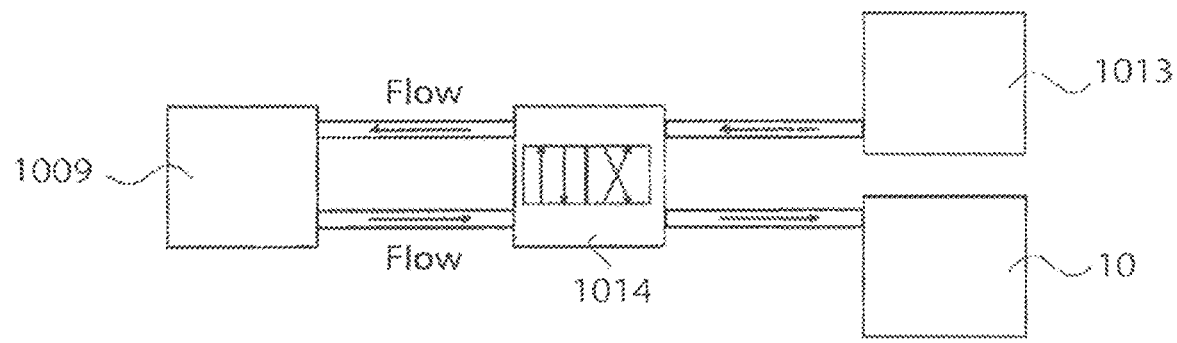
FIGS. 39-42 show various ways of arranging hydraulic or pneumatic powering of an apparatus implanted in a patient.

FIG. 39 shows a system as described above with. The system comprises an implanted apparatus 10 and further a separate regulation reservoir 1013, a one way pump 1009 and an alternate valve 1014.

Figure 40:
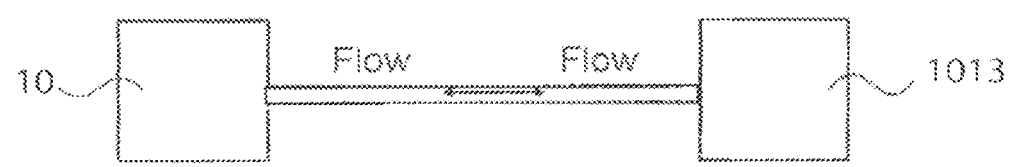

FIG. 40 shows the apparatus 10 and a fluid reservoir 1013. By moving the wall of the regulation reservoir or changing the size of the same in any other different way, the adjustment of the apparatus may be performed without any valve, just free passage of fluid any time by moving the reservoir wall.

Figure 41:
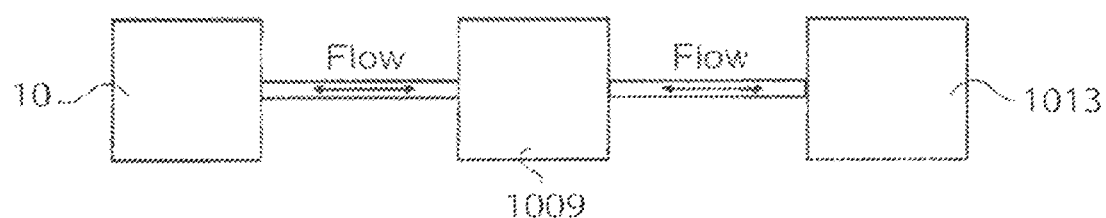

FIG. 41 shows the apparatus 10, a two way pump 1009 and the regulation reservoir 1013.

Figure 42:
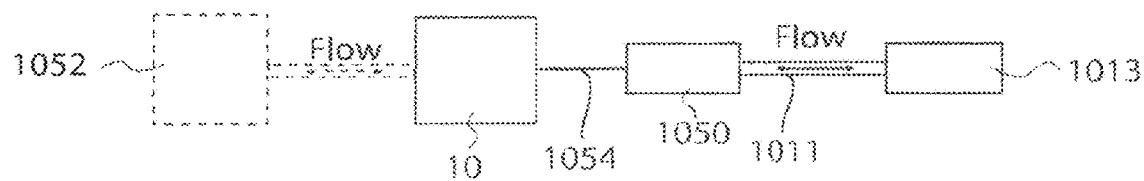

FIG. 42 shows a block diagram of a reversed servo system with a first closed system controlling a second closed system. The servo system comprises a regulation reservoir 1013 and a servo reservoir 1050. The servo reservoir 1050 mechanically controls an implanted apparatus 10 via a mechanical interconnection 1054. The apparatus has an expandable/contactable cavity. This cavity is preferably expanded or contracted by supplying hydraulic fluid from the larger adjustable reservoir 1052 in fluid connection with the apparatus 10. Alternatively, the cavity contains compressible gas, which can be compressed and expanded under the control of the servo reservoir 1050. The servo reservoir 1050 can also be part of the apparatus itself.

Figure 43A:
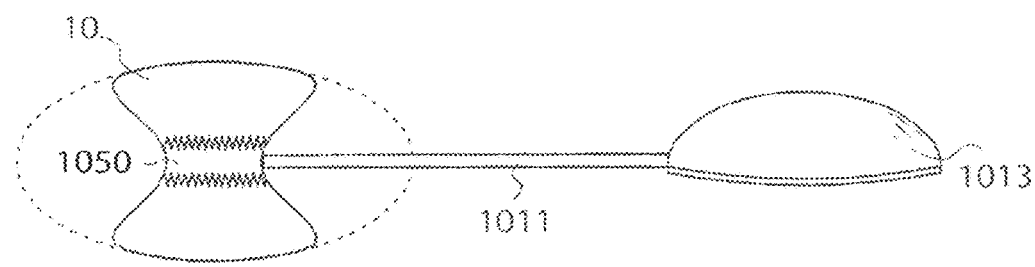
FIGS. 43a-c show various ways of arranging hydraulic or pneumatic powering of an apparatus implanted in a patient.
Figure 43B:
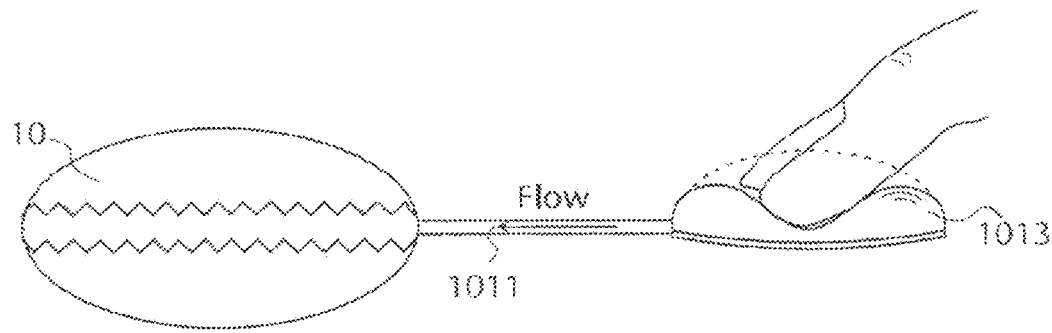
Figure 43C:
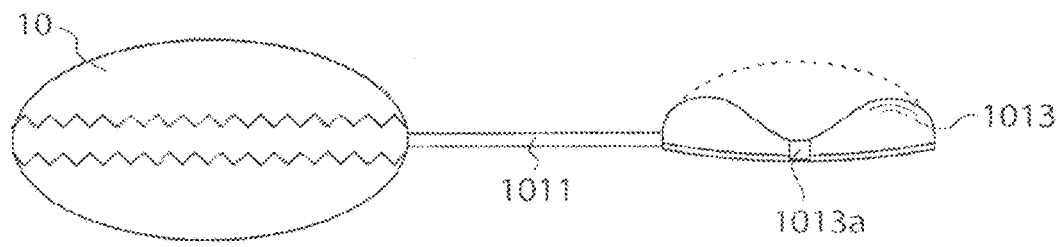
Figure 44:
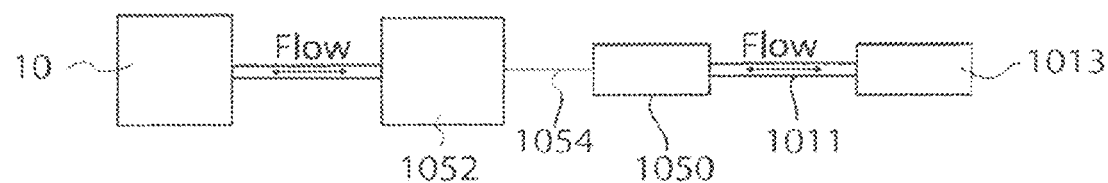
FIG. 44 show various ways of arranging hydraulic or pneumatic powering of an apparatus implanted in a patient.

In one embodiment, the regulation reservoir is placed subcutaneous under the patient's skin and is operated by pushing the outer surface thereof by means of a finger. This system is illustrated in FIGS. 43a-c. In FIG. 43a, a flexible subcutaneous regulation reservoir 1013 is shown connected to a bulge shaped servo reservoir 1050 by means of a conduit 1011. This bellow shaped servo reservoir 1050 is comprised in a flexible apparatus 10. In the state shown in FIG. 43a, the servo reservoir 1050 contains a minimum of fluid and most fluid is found in the regulation reservoir 1013. Due to the mechanical interconnection between the servo reservoir 1050 and the apparatus 10, the outer shape of the apparatus 10 is contracted, i.e., it occupies less than its maximum volume. This maximum volume is shown with dashed lines in the figure.

FIG. 43b shows a state wherein a user, such as the patient in with the apparatus is implanted, presses the regulation reservoir 1013 so that fluid contained therein is brought to flow through the conduit 1011 and into the servo reservoir 1050, which, thanks to its bellow shape, expands longitudinally. This expansion in turn expands the apparatus 10 so that it occupies its maximum volume, thereby stretching the stomach wall (not shown), which it contacts.

The regulation reservoir 1013 is preferably provided with means 1013a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 44 and 45a-c. The block diagram shown in FIG. 44 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted apparatus 10 having an expandable/contactable cavity is in turn controlled by the larger adjustable reservoir 1052 by supply of hydraulic fluid from the larger adjustable reservoir 1052 in fluid connection with the apparatus 10.

Figure 45A:
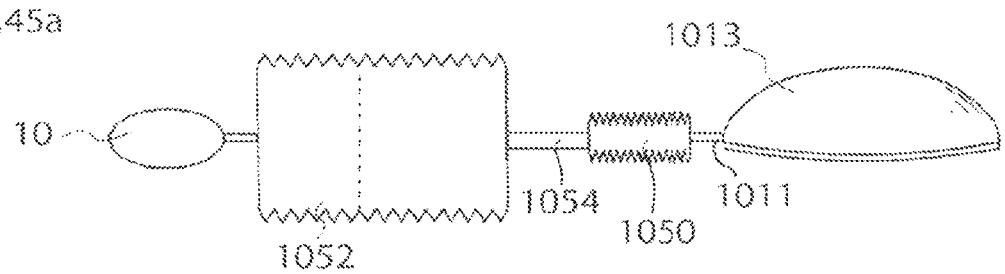
FIGS. 45a-c show various ways of arranging hydraulic or pneumatic powering of an apparatus implanted in a patient.
Figure 45B:
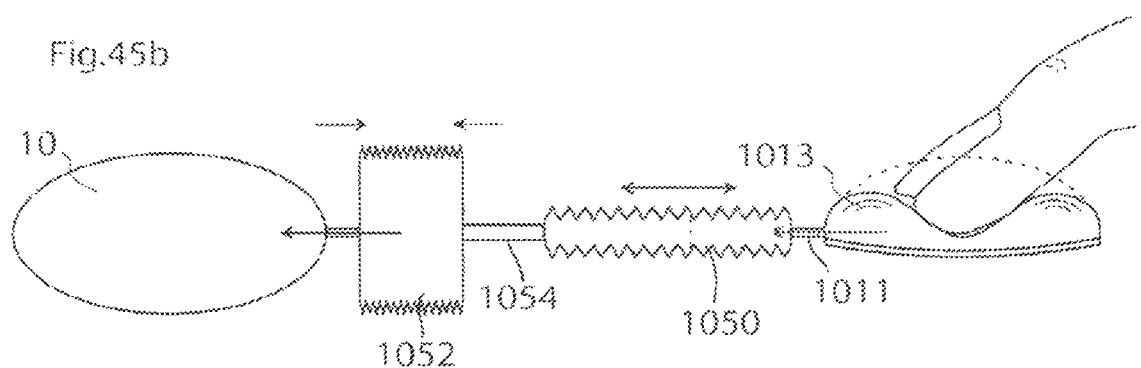
Figure 45C:
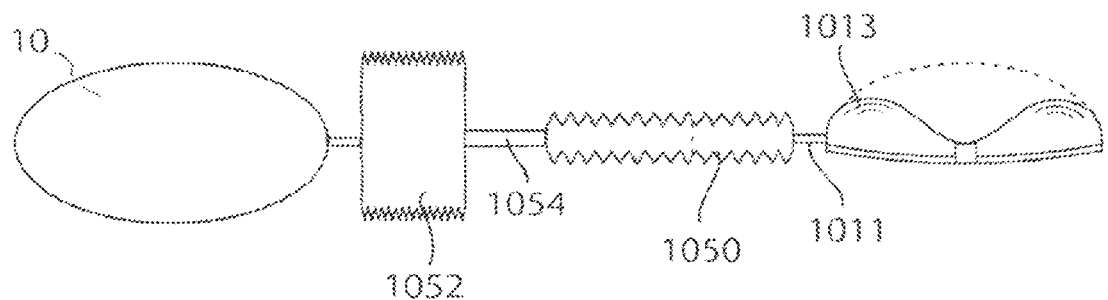

An example of this embodiment will now be described with reference to FIG. 45a-c. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 45a, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the apparatus 10. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the apparatus 10. In other words, in this reversed servo, a small volume in the regulation reservoir is compressed with a higher force and this creates a movement of a larger total area with less force per area unit.

Like in the previous embodiment described above with reference to FIGS. 43a-c, the regulation reservoir 1013 is preferably provided with means 1013a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

Figure 46:
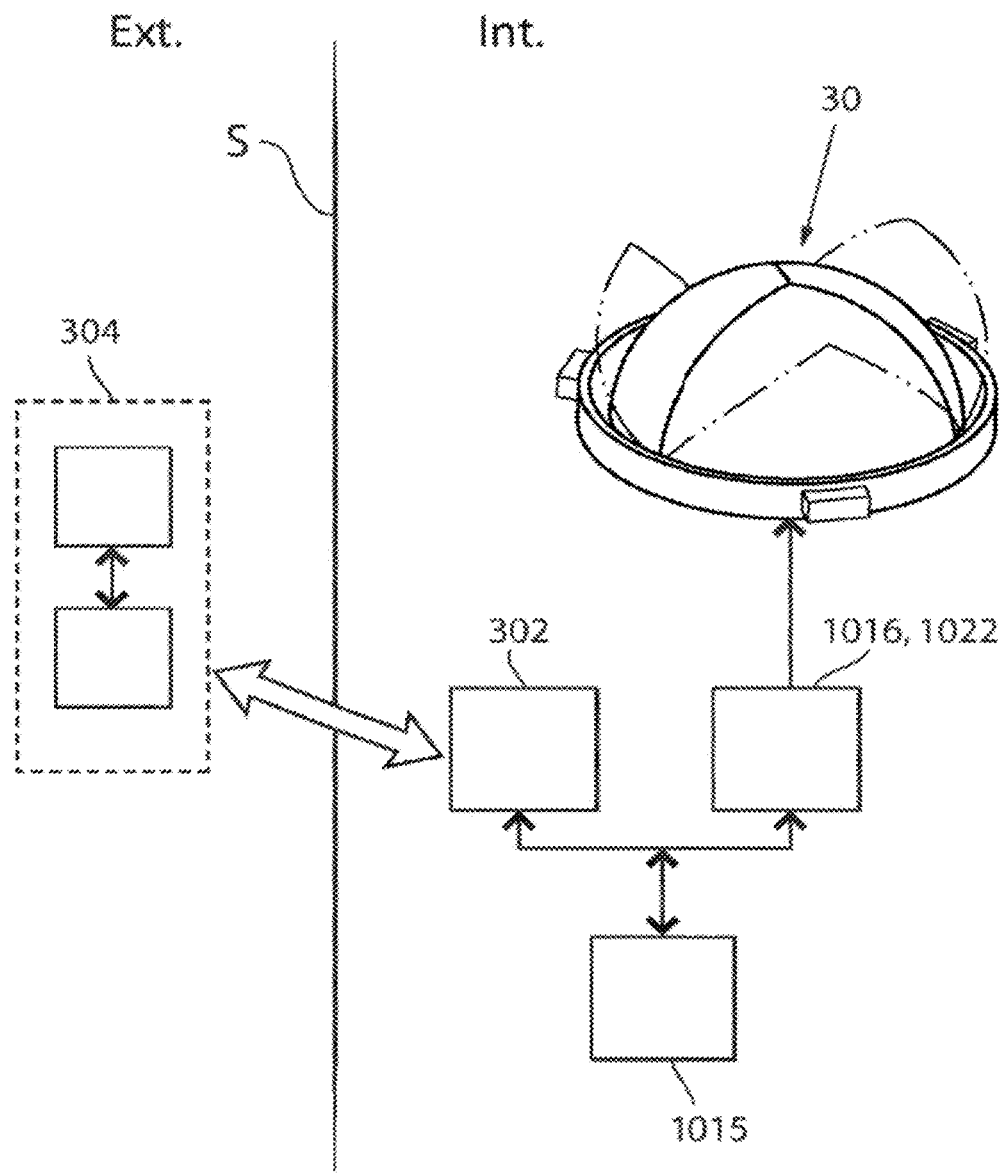
FIG. 46 shows a system of the invention.

FIG. 46 shows a system of the invention, with the skin of a patient being shown as "S", and with an apparatus 30 of the invention being implanted into a patient, "Int", and with other details on the outside of the patient, "Ext"

Besides the apparatus 30, the implanted equipment comprises an energy transforming device 302 as described above, a battery 1022 and, as an alternative or complement, an accumulator 1016, with both the energy transforming device and the battery/accumulator being controlled by the control device 1015.

The "external equipment" comprises a remote control, which is shown as possibly comprising two parts, i.e. a transmitter or transceiver for transmitting and possibly receiving energy to/from the device 302, and a remote control I, which may be integrated into one physical unit together with the transmitter or transceiver.

The invention also discloses a method as follows:

A. A method of surgically placing a valve of the invention in a patient's heart or blood vessel via a laparoscopic thoracic approach, the method comprising the steps of:
  inserting a needle or a tube like instrument into the thorax of the patient's body,
  using the needle or a tube like instrument to fill the thorax with gas thereby expanding the thoracic cavity,
  placing at least two laparoscopic trocars in the patient's body,
  inserting a camera through one of the laparoscopic trocars into the thorax,
  inserting at least one dissecting tool through one of said at least two laparoscopic trocars and dissecting an intended placement area of the patient,
  placing the valve in any part of the blood stream in the thorax, and
  placing and connecting an implanted energy receiver or source of energy for powering the valve to perform at least one of the following method steps;
  at least partly closing and at least partly opening of the valve.

B. An operation method for surgically placing a valve of the invention in a patient's heart or blood vessel, the method comprising the steps of:
  cutting the patient's skin,
  opening the thoracic cavity,
  dissecting a placement area where to place the valve inside a blood stream in the heart, or the aorta or inside the pulmonary artery of the human patient,
  placing the a valve in the placement area in any part of the blood stream in the thorax, and
  placing and connecting an implanted energy receiver or a source of energy for powering the valve to perform at least one of the following method steps;
  at least partly closing and at least partly opening of the valve.

C. A method of surgically placing a valve of the invention in a patient's heart or blood vessel via a laparoscopic abdominal approach, the method comprising the steps of:
  inserting a needle or a tube like instrument into the abdomen of the patient's body,
  using the needle or a tube like instrument to fill the thorax with gas thereby expanding the abdominal cavity,
  placing at least two laparoscopic trocars in the patient's abdomen
  inserting a camera through one of the laparoscopic trocars into the abdomen,
  inserting at least one dissecting tool through one of said at least two laparoscopic trocars and
  dissecting and creating an opening in the diaphragm muscle,
  dissecting an intended placement area of the patient through said opening,
  placing the valve in any part of the blood stream in the thorax, and
  placing and connecting an implanted energy receiver or source of energy for powering the valve to perform at least one of the following method steps;
  at least partly closing and at least partly opening of the valve.

D. An operation method for surgically placing a valve of the invention in a patient's heart or blood vessel, the method comprising the steps of:
  cutting the patient's skin,
  opening the abdominal cavity,
  dissecting and creating an opening in the diaphragm muscle,
  dissecting a placement area where to place the valve inside a blood stream in the heart, or the aorta or inside the pulmonary artery of the human patient through said opening,
  placing the a valve in the placement area, and
  placing and connecting an implanted energy receiver or a source of energy for powering the valve to perform at least one of the following method steps;
  at least partly closing and at least partly opening of the valve.

E. An operation method for surgically placing a valve of the invention in a patient's heart or blood vessel, via inguinal key-hole surgery approach, the method comprising the steps of:
  cutting the patients skin,
  inserting a needle or a tube like instrument into the inguinal area of the patient's body,
  using the needle or a tube like instrument to fill a cavity with gas thereby expanding the cavity,
  placing at least two laparoscopic trocars in the patient's cavity
  inserting a camera through one of the trocars into the cavity,
  inserting at least one dissecting tool through one of said at least two trocars and
  dissecting the area of the femoral artery,
  inserting a tube like instrument into the femoral artery of the patient's body,
  inserting said valve into the femoral artery,
  using said instrument to guide said valve through the femoral artery to the aorta or heart of the patient,
  releasing the valve inside of a blood vessel or heart
  placing said valve in the blood vessel or heart,
  placing and connecting an implanted energy receiver or a source of energy for powering the valve to perform at least one of the following method steps;
  at least partly closing and at least partly opening of the valve.

F. An operation method for surgically placing a valve of the invention in a patient's heart or blood vessel, via a inguinal approach, the method comprising the steps of:
  cutting the patients skin,
  dissecting the inguinal region,
  dissecting the area of the femoral artery,
  inserting a tube like instrument into the femoral artery of the patient's body,
  using said instrument to guide said rotating body through the femoral artery and the aorta to the blood vessel or heart,
  releasing the valve inside of the heart or blood vessel,
  placing said valve in the blood vessel or heart, placing and connecting an implanted energy receiver or a source of energy for powering the valve to perform at least one of the following method steps;

at least partly closing and at least partly opening of the valve.

G. In one embodiment of the invention according to any of items A-F, the step of placing the valve additionally comprises the step of:

placing a drive unit for at least partly powering the valve movements in the placement area, inside the blood stream of the blood vessel, inside the heart, or the aorta or inside the pulmonary artery of the patient, supplying energy from said drive unit to said valve causing movement of said valve.

H. In one embodiment of the invention according to any of items A-F, the step of placing the valve additionally comprises the step of:

placing a drive unit for at least partly powering the valve movements in the placement area, outside the blood stream of the blood vessel, outside the heart, or the aorta or outside the pulmonary artery of the patient, placing said drive unit on the outside of said valve, supplying energy from said drive unit to said valve causing movement of said valve.

I. In one embodiment of the invention according to items I or H, the step of supplying energy from said drive unit to said valve, causing movement of said valve, additionally comprises the step of:

supplying wireless or magnetic energy from said drive unit to said valve, causing movement of said valve.

J. In one embodiment of the invention according to any of items G-I, the method additionally comprises the step of:

connecting the drive unit with the energy receiver or source of energy for powering said drive unit.

K. In one embodiment of the invention according to any of items A-D and H, for parts of the valve placed outside the blood stream, combining with the method according to one or more of claims E-G for parts of the valve placed inside the blood stream.

L. In one embodiment of the invention according to item J, said drive unit placed outside the blood stream comprises a stator, and the part of the valve placed inside the blood stream comprises a rotor, wherein said stator supplies wireless energy to said part of the valve placed inside the blood stream, causing rotational movement of at least a part of said drive unit.

M. In one embodiment of the invention according to item L, the drive unit further comprises both said rotor adapted to be placed outside the blood stream, said rotor comprising a magnetic coupling for driving at least a part of the valve placed inside the blood stream with rotational energy, the method further comprising the steps of:

placing said stator and rotor on the outside of said valve including a magnetic coupling in the placement area, wherein said rotor comprises said magnetic coupling, adapted to be magnetically connecting to said valve placed inside the blood stream, supplying energy to said stator to rotate said rotor and thereby rotating said valve, thereby causing, through the magnetic coupling, rotating movement of said valve.

N. In one embodiment of the invention according to any of items A-M, an opening is performed from the abdomen through the thoracic diaphragm for placing the energy receiver or energy source in the abdomen.

O. In one embodiment of the invention according to any of items C, D and N, said opening is performed in the thoracic diaphragm at the place where the pericardium is attached to the thoracic diaphragm.

P. In one embodiment of the invention according to any of items A-O, the valve or drive unit uses energy, direct or indirect, from an external energy source, supplying energy non-invasively, without any penetration through the patient's skin to power the valve or drive unit.

Q. In one embodiment of the invention according to any of items A-H, said valve or drive unit is connected to an internal energy source via a cable, the method of placement further comprising;

dissecting and placing a wire connected to the valve or drive unit into the right atrium of the heart and further up in the venous blood vessel system, exiting the system in or closer to the subcutaneous area, such as in the vena subclavia, vena jugularis or vena brachialis placing an internal energy source in the subcutaneous area or close thereto or in the thorax or abdomen, supplying from an external energy source energy non-invasively, without any penetration through the patient's skin to power the internal energy source for indirect or direct power the valve or drive unit.

R. In one embodiment of the invention according to any of items A-H, the method of placement further comprises;

placing an electrode in the right atrium or ventricle of the heart placing the wire to the electrode via the right atrium of the heart and further up in the venous blood vessel system, exiting the blood vessel system in or closer to the subcutaneous area, such as in the vena subclavia, vena jugularis or vena brachialis, placing an internal control unit in the subcutaneous area or close thereto or in the thorax or abdomen, the method further comprising at least one of the following steps;

receiving sensor input relating to electrical pulses or muscle contractions of the heart or transmitting energy pulses from said electrode for controlling heart contractions, coordinating the valve or drive unit.

In various embodiments, the artificial valve of the invention also exhibits the following features:

A. The artificial valve is adapted to pass through a laparoscopic trocar in the patient's body.

B. The artificial valve is adapted to pass through an opening in the diaphragm muscle from the abdominal side.

C. The artificial valve is adapted to be inserted into the femoral artery and is further adapted to be released inside of the heart or blood vessel.

D. The artificial valve of item A, also comprising a drive unit for at least partly powering the valve movements, adapted to be placed inside the blood stream including a blood vessel or heart.

E. The artificial valve of item A, comprising a drive unit for at least partly powering the valve movements, adapted to be placed outside the blood stream including a blood vessel or heart.

F. The artificial valve of items D or E, wherein said drive unit is adapted to supply wireless or magnetic energy, said valve being adapted to receive said wireless or magnetic energy to cause movements of said valve.

G. The artificial valve of item D or E, wherein said drive unit comprises a stator, adapted to be placed outside the blood stream, the blood vessel or heart, and further comprising a rotor adapted to be placed inside the blood stream, wherein said stator is adapted to supply wireless or magnetic energy to the rotor placed inside the blood stream, causing movements of at least a part of said valve placed inside the blood stream.

H. The artificial valve of item D or E, wherein said drive unit comprises a stator and a rotor, adapted to be placed outside the blood stream, the blood vessel or heart, said rotor comprising a magnetic coupling for driving at least a part of the valve placed inside the blood stream with kinetic energy.

I. The artificial valve of item A, wherein an energy receiver or energy source is adapted to be placed in the abdomen.

J. The artificial valve of item D or E, comprising an electric wire adapted to connect said valve or drive unit to an internal energy source, said wire adapted to pass into the right atrium of the heart and further up in the venous blood vessel system, exiting the blood vessel system in or closer to the subcutaneous area, wherein said internal energy source is adapted to be connected to said wire via the subcutaneous area.

K. The artificial valve of item A, comprising;
an internal control unit,
a sensor sensing physiological electrical pulses or muscle contractions of the heart,
wherein said control unit controls said valve according to the sensed information.

L. The artificial valve of item J:
in which said internal energy source comprises an internal control unit adapted to transmit energy pulses to said electrode for achieving and controlling heart contractions, wherein said control unit is adapted to coordinate the valve or drive unit.

The invention is not limited to the examples of embodiments described above and shown in the drawings, but may be freely varied within the scope of the appended claims.

The invention claimed is:

1. An artificial valve for implantation in a mammal body, in or adjacent to a mammal blood vessel, the artificial valve comprising a casing and a closing mechanism, with at least part of said closing mechanism being a first moving part adapted to make movements relative to said casing, said movements being movements to assume an open and a closed position for opening and closing, respectively, blood flow through said blood vessel, as well as at least one position in between said open and said closed positions, characterized in that the first moving part is adapted to receive energy for at least one of its movements at least in part from an energy device which is also comprised in the artificial valve and arranged to be placed external to said blood vessel, wherein the closing mechanism comprises two or more magnets and at least one coil which are adapted to interact to cause at least one of said movements of the closing mechanism, wherein the at least one coil is connected to the energy device and arranged to receive a current so as to interact electromagnetically with the two or more magnets being arranged at a position on the moving part, thereby causing the at least one of said movements of the closing mechanism.

2. The valve of claim 1, in which said magnets of the closing mechanism are adapted to receive energy from the energy device as a first pulse, said two or more magnets further being adapted to receive one or more additional pulses with a time delay in relation to said first pulse to cause said movement of said first moving part.

3. The valve of claim 1, in which at least either the magnets, or the at least one coil are arranged at intervals in the casing along an intended path of movement of the moving part.

4. The artificial valve of claim 1, in which valve the first moving part of the closing mechanism is adapted to assume a position at least partly placed outside of the blood vessel when the valve is in a non-closed position in the mammal body.

5. The artificial valve of claim 1, in which the first moving part is adapted to, when the valve is arranged in or adjacent to an opening in said blood vessel, move in the opening in the blood vessel to limit or close the blood flow through said vessel, with at least a portion of said first moving part assuming a position external to said blood vessel in a non-closed position.

6. The artificial valve of claim 5, in which the first moving part is arranged to move in said opening in a direction which is essentially perpendicular to an extension of the blood vessel.

7. The valve of claim 5, in which said first moving part is given a curved or semicircular shape at an end of the first moving part which will be the first to enter said opening in the blood vessel during a closing movement of the first moving part, whereby the first moving part is adapted to fit against a distal inner wall of the blood vessel in order to close or limit the blood flow in said blood vessel.

8. The artificial valve of claim 1, in which the first moving part comprises an elongated essentially flat plate which is adapted to, when the valve is arranged in or adjacent to an opening in said blood vessel, move in a direction essentially perpendicular to said blood vessel to limit or close the blood flow through said vessel, with at least a portion of said first moving part assuming a position external to said blood vessel in a non-closed position.

9. The artificial valve of claim 1, in which the closing mechanism is housed in the casing, with the first moving part being adapted to protrude from the housing in its closing movement.

10. The valve of claim 1, also comprising a biasing mechanism for biasing the plate to an open position wherein said biasing mechanism comprises a spring mechanism.

11. The valve of claim 1, in which the casing also comprises at least a first curved protruding part for surrounding at least part of a circumference of the blood vessel for attachment of the valve to said blood vessel.

12. The valve of claim 1, in which the casing also comprises at least first and second curved protruding parts for surrounding at least part of a circumference of the blood vessel, for attachment of the valve to said blood vessel.

13. The valve of claim 11, in which the protruding part or parts, together with a concave outer wall, are adapted to be attached to the blood vessel by means of a vascular graft.

14. An artificial valve for implantation in a mammal body, in or adjacent to a mammal blood vessel, the artificial valve comprising a casing and a closing mechanism, with at least part of said closing mechanism being a first moving part adapted to make movements relative to said casing, said movements being movements to assume a open and a closed position for opening and closing, respectively, blood flow through said blood vessel, as well as at least one position in between said open and said closed positions, characterized in that the first moving part is adapted to receive energy for at least one of its movements at least in part from an energy device which is also comprised in the artificial valve and arranged to be placed external to said blood vessel, wherein the closing mechanism comprises two or more magnets and at least one coil which are adapted to interact to cause at least one of said movements of the closing mechanism, wherein the at least one coil is connected to the energy device and arranged to receive a current so as to interact electromagnetically with the two or more magnets, the at least one coil being arranged at a position on the moving part, thereby causing the at least one of said movements of the closing mechanism.

* * * * *